United States Patent [19]

Honda et al.

[11] Patent Number: 5,834,575
[45] Date of Patent: Nov. 10, 1998

[54] COMPOUNDS AND POLYMERS, RESIN COMPOSITIONS, NONLINEAR OPTICAL ELEMENT AND NONLINEAR OPTICAL DEVICES, AND PRODUCTION PROCESS THEREFOR

[75] Inventors: Yutaka Honda, Tsuchiura; Iwao Fukuchi, Tsukuba; Masato Taya, Hitachi, all of Japan; Kwan-Yue Alex Jen, Morganville, N.J.

[73] Assignee: Hitachi Chemical Company, Ltd., Japan

[21] Appl. No.: 747,877

[22] Filed: Nov. 13, 1996

[51] Int. Cl.$^6$ .............................. C08F 28/06; C08F 26/06
[52] U.S. Cl. .................. 526/256; 526/328; 526/329.7; 525/326.7; 525/327.1; 525/328.5; 525/329.1; 525/330.4; 525/348; 525/421; 525/426; 528/337; 528/341; 528/345; 528/352; 528/362; 528/364; 528/380; 528/347; 252/182.17; 430/630
[58] Field of Search ................. 549/75, 60; 526/256, 526/328, 329.7; 525/326.7, 327.1, 328.5, 329.1, 329.2, 329.4, 330.4, 348, 421, 426; 528/337, 341, 345, 347, 362, 364, 352, 353, 380; 252/182.17; 430/630

[56] References Cited

U.S. PATENT DOCUMENTS

| | | | |
|---|---|---|---|
| 3,978,029 | 8/1976 | Limburg | 428/500 |
| 4,892,681 | 1/1990 | Miyata et al. | 252/582 |
| 4,894,186 | 1/1990 | Gordon et al. | 252/582 |
| 4,894,263 | 1/1990 | Dubois et al. | 428/1 |
| 4,933,112 | 6/1990 | De Martino et al. | 252/587 |
| 4,935,292 | 6/1990 | Marks et al. | 428/220 |
| 4,946,629 | 8/1990 | Allen et al. | 252/589 |
| 4,981,614 | 1/1991 | Miyazaki et al. | 252/587 |
| 4,985,325 | 1/1991 | Kuroda et al. | 430/59 |
| 5,061,404 | 10/1991 | Wu et al. | 252/502 |
| 5,156,774 | 10/1992 | Leising et al. | 252/582 |
| 5,395,556 | 3/1995 | Drost et al. | 252/582 |
| 5,514,799 | 5/1996 | Varanasi et al. | 544/300 |

FOREIGN PATENT DOCUMENTS

| | | |
|---|---|---|
| 637774 | 2/1995 | European Pat. Off. . |
| 0 647 874 A1 | 4/1995 | European Pat. Off. . |
| 6-157511 | 6/1994 | Japan . |
| 7-173116 | 7/1995 | Japan . |
| 7-196795 | 8/1995 | Japan . |

OTHER PUBLICATIONS

K.J.Drost et al., "A new synthetic approach for the incorporation of highly efficient second-order nonlinear optical chromophores containing tricyanovinyl electron acceptors into methacrylate polymers", J.Chem.Soc.Chem.Commun., 1994 (4), pp. 369–371.

M.A.Pauley et al., "Hyper–Rayleigh scattering studies of first order hyperpolarizability of tricyanovinylthiophene derivatives in solution", J.Chem.Phys. 102(16), 22 Apr., 1995, pp. 6400–6405.

M.A.Pauley et al., "Determination of first hyperpolarizability of nonlinear optical chromophores by second harmonic scattering using an external reference ", J.Chem.Phys. 104 (20), 22 May 1996 pp. 7821–7829.

V.P.Rao et al., "Achieving excellent tradeoffs among optical, chemical and thermal properties in second–order nonlinear optical chromophores", J.Chem.Commun., 1996 (10), pp. 1237–1238.

(List continued on next page.)

*Primary Examiner*—Deborah C. Lambkin
*Attorney, Agent, or Firm*—Pennie & Edmonds LLP

[57] ABSTRACT

As a heteroaromatic compound made functional so as to be used in nonlinear optical materials, the present invention provides a heteroaromatic compound represented by the following Formula (1), (2), (3) or (4), a polymer obtained from any of these, a nonlinear optical element comprised of the polymer, an optical device having such an element, and a process for producing them.

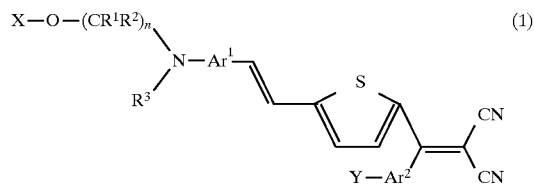

(1)

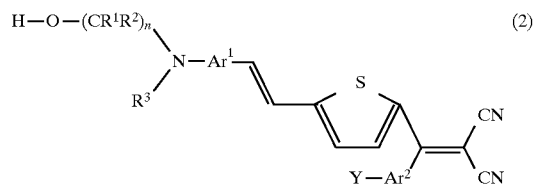

(2)

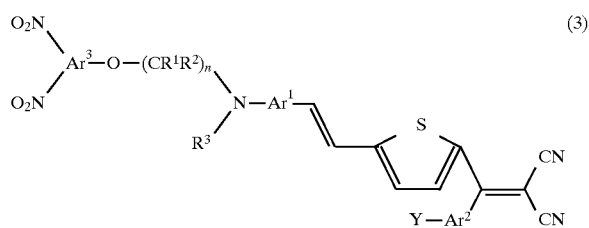

(3)

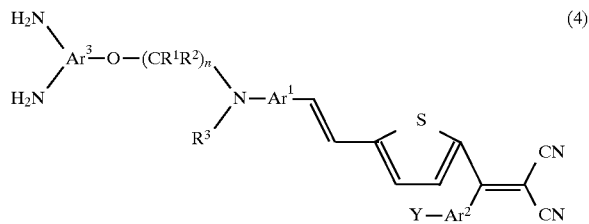

(4)

wherein $Ar^1$, $Ar^2$ and $Ar^3$ each independently represent an aromatic group or an aromatic group having a substituent, $R^1$, $R^2$ and $R^3$ each independently represent a hydrogen atom or a monovalent organic group, X represents a monovalent organic group, Y represents a hydrogen atom or a monovalent functional group, and n represents an integer of 2 to 10.

26 Claims, 8 Drawing Sheets

OTHER PUBLICATIONS

F. Wang et al., "Design and synthesis of a perfluoroalkyld-lcyanovinyl–based NLO material for electro–optic applications", Polym. Prepr., 1997 38(1), pp. 971–972.

Dirk, "Third Order Nonlinear Optical Molecules and the Two Level Model", Proc. SPIE–Int. Soc. Opt. Eng., 1147:18–25 (1989).

FIG. 2
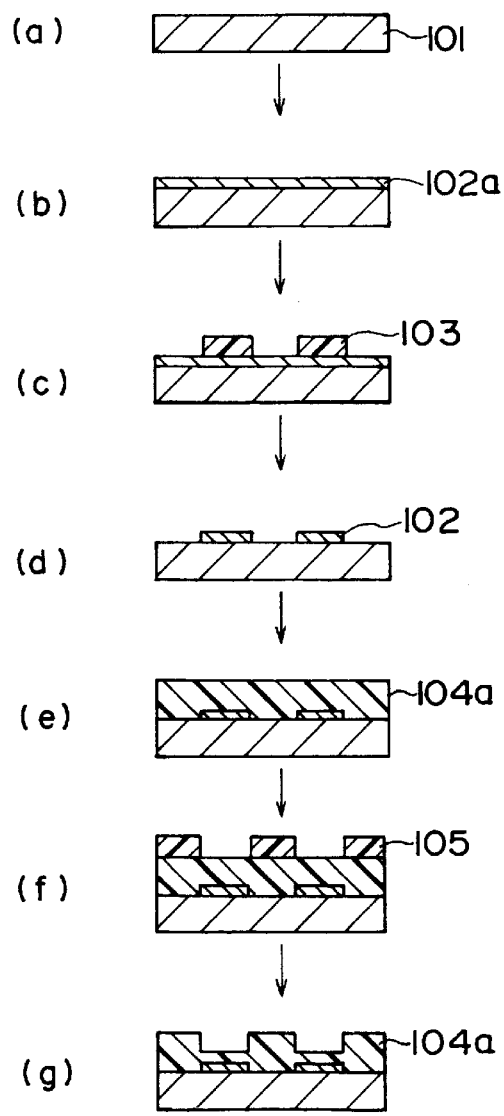
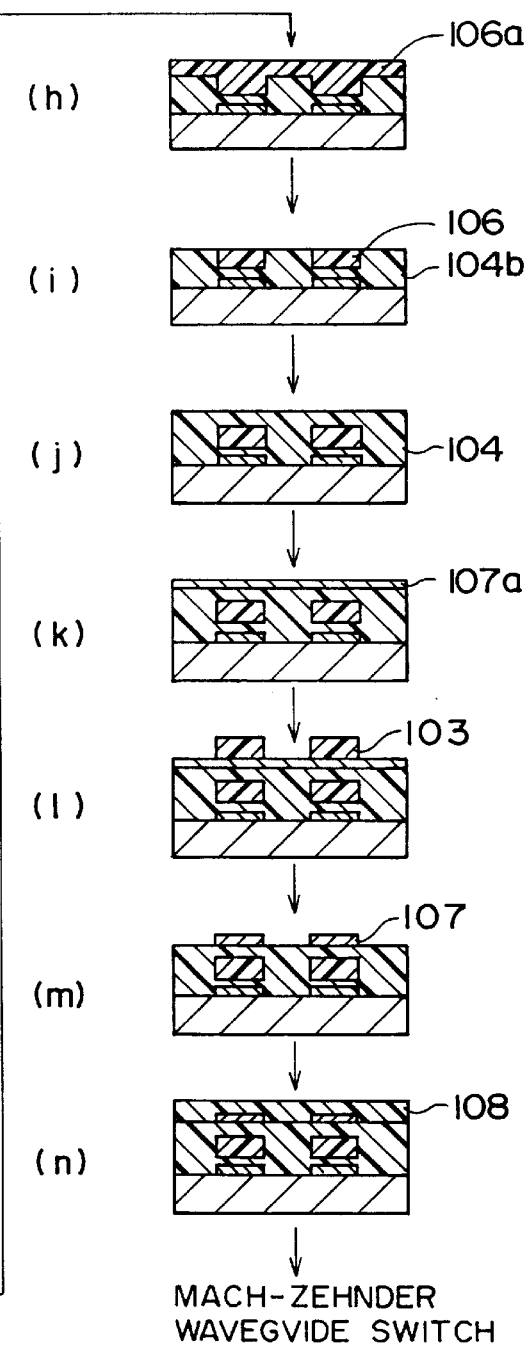
MACH-ZEHNDER
WAVEGVIDE SWITCH

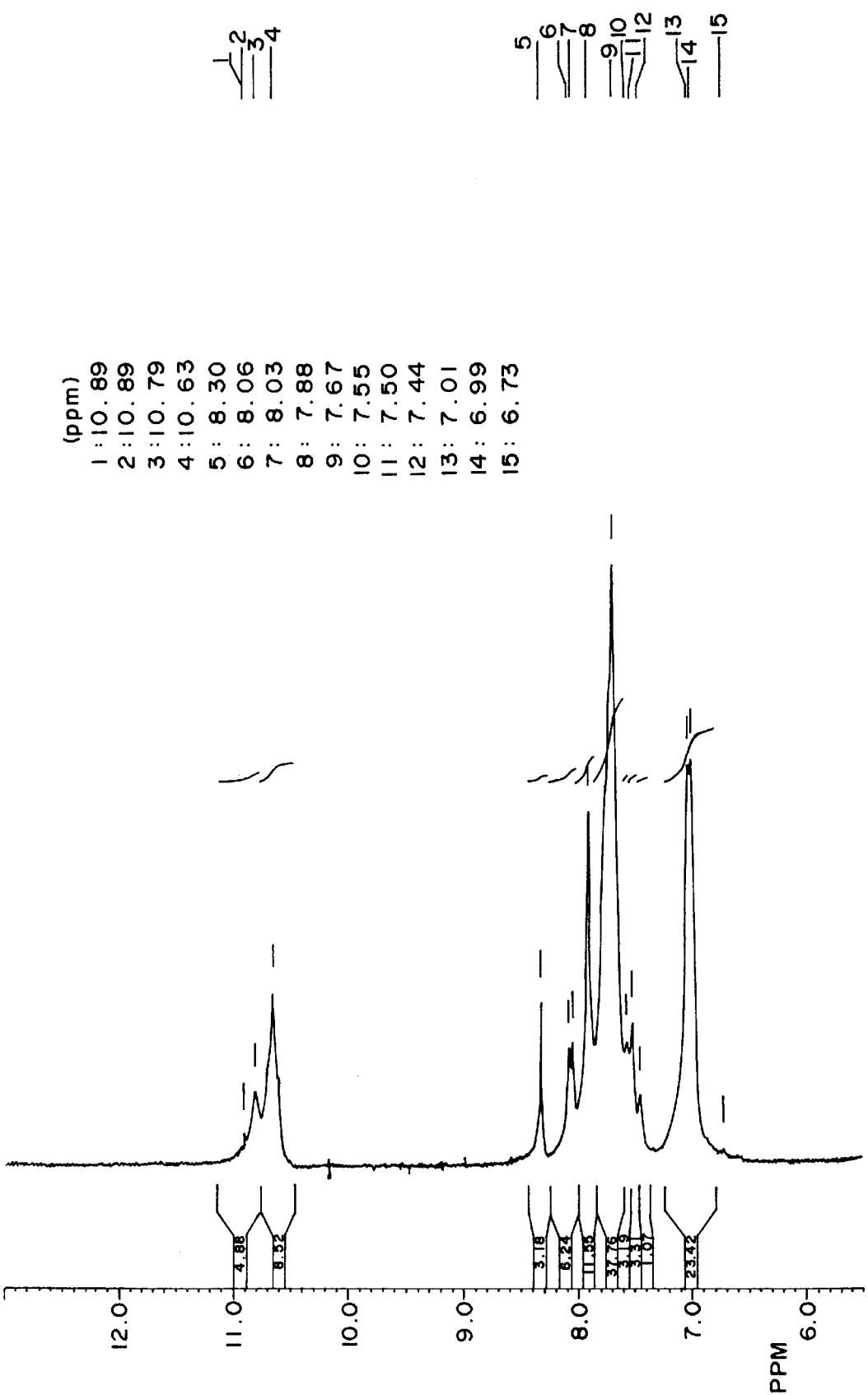

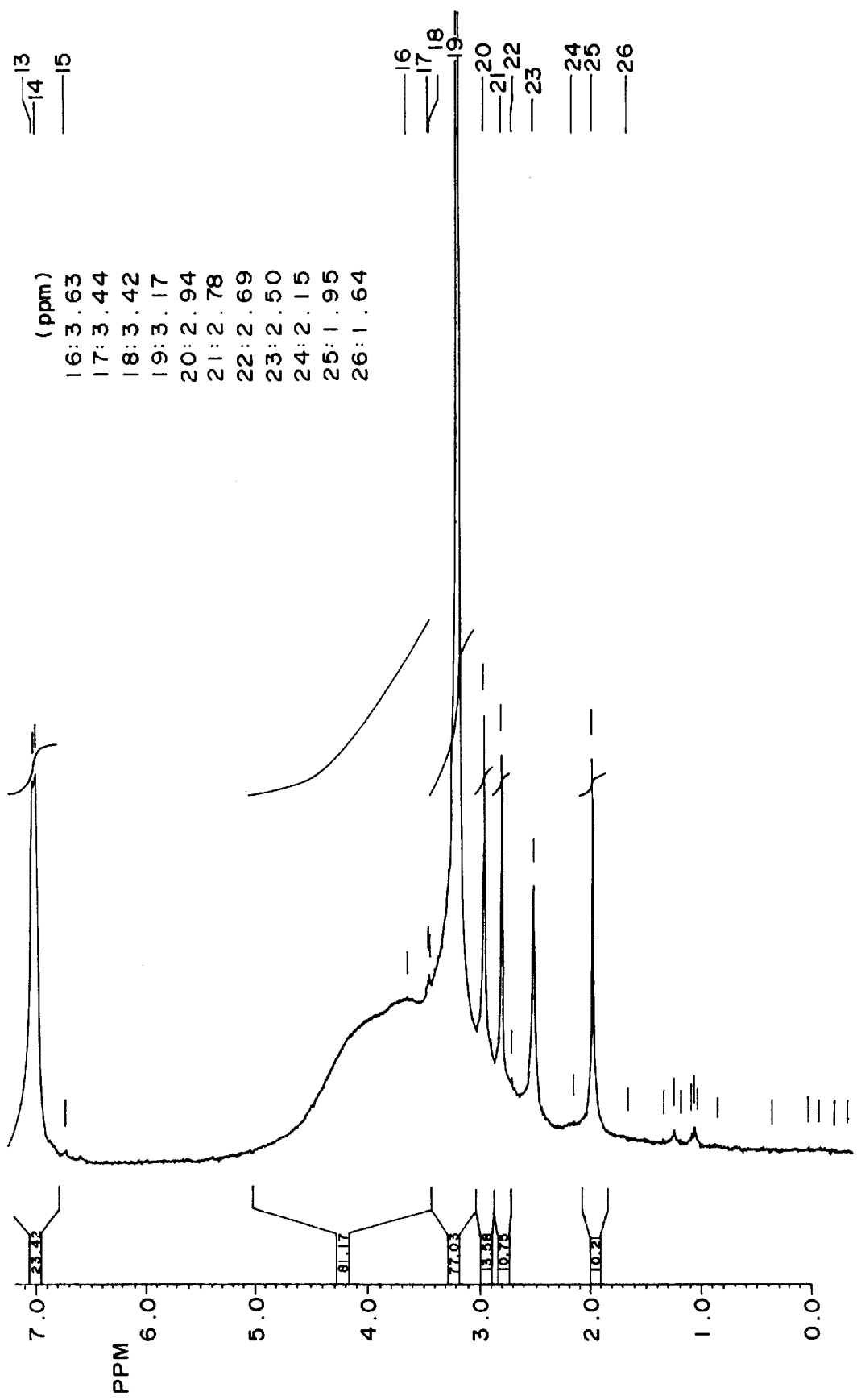

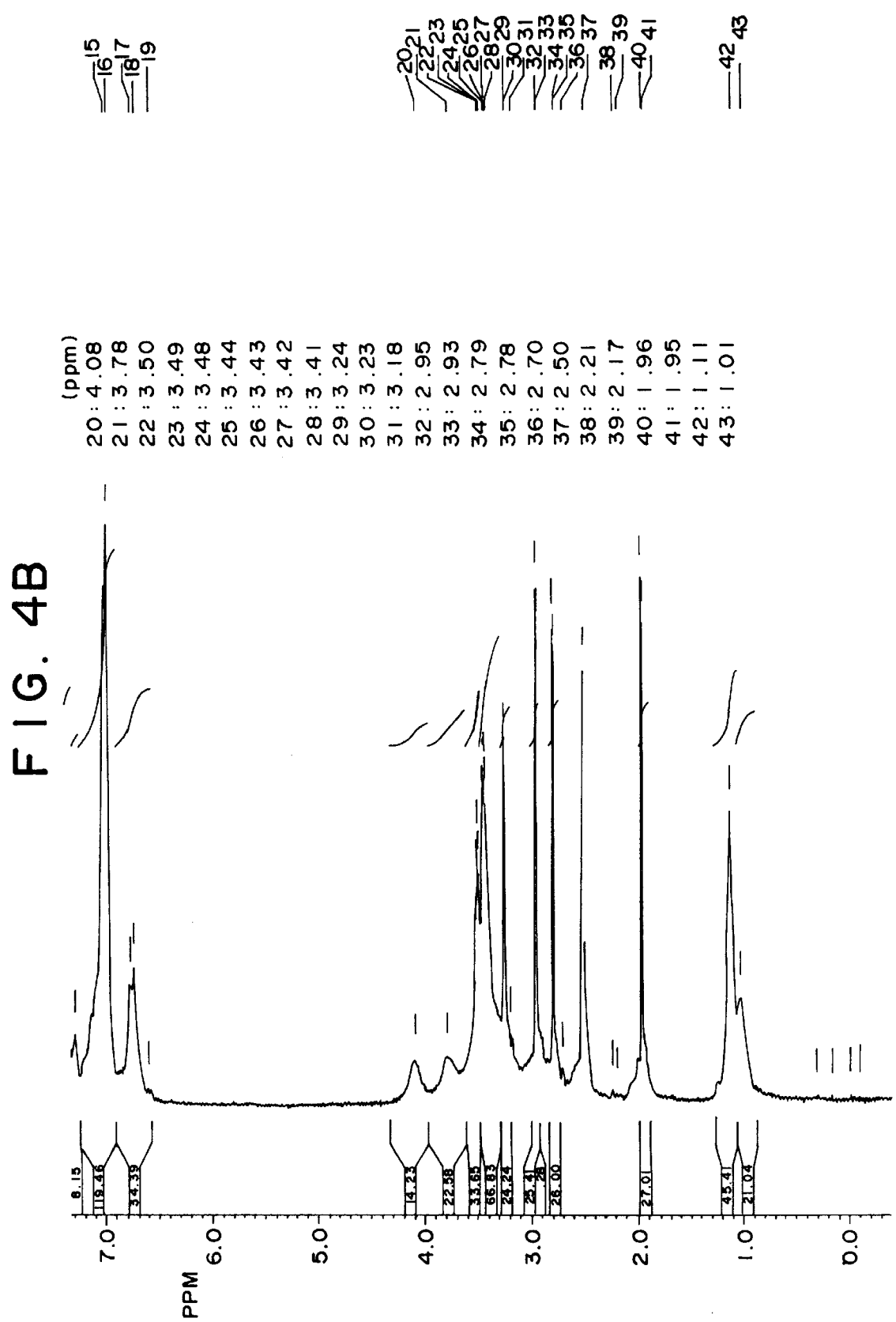

COMPOUNDS AND POLYMERS, RESIN COMPOSITIONS, NONLINEAR OPTICAL ELEMENT AND NONLINEAR OPTICAL DEVICES, AND PRODUCTION PROCESS THEREFOR

BACKGROUND OF THE INVENTION

1. Field of the Invention

This invention relates to a compound and a polymer which have nonlinear optical activities, processes for producing them, a resin composition containing them, a nonlinear optical element prepared using the resin composition, and a nonlinear optical device having the element.

2. Prior Art

Nowadays, materials having nonlinear optical activities (NLO materials) suffuciently highly effective to double or triple the frequency of electromagnetic waves attract great scientific and technical interest as materials usable in optical long-distance communication, signal processing, photoelectric hybrid circuits and optical computers.

Nonlinear optics is concerned with the mutual action of electromagnetic waves in various mediums, which is necessary for generating a new field variable in frequency or amplitude, and electro-optic adjustment of electromagnetic waves is represented by, e.g., the following two expressions.

$$\Delta n = -(\tfrac{1}{2}) n^3 r_{33} E$$

$$r_{33} \propto \beta\mu$$

In the above, $\Delta n$ is change in refractive index, n is refractive index, $r_{33}$ is electro-optic constant, E is electric-field strength, $\beta$ is secondary nonlinear susceptibility, and $\mu$ is dipole moment. The $r_{33}$ increases with an increase in $\beta\mu$, and therefore $\Delta n$ increases with $\beta\mu$.

In Proc. SPIE-Int. Soc. Opt. Eng., 1147, 18–25 (1989), Dirk reports that an azomethine-derived chromophore containing a heteroaromatic ring of 5 members has a ternary NLO susceptibility. Japanese Patent Applications Laid-open KOKAI No. 6-157511 and No. 7-173116 also disclose an NLO material having a secondary nonlinear susceptibility, comprised of a thiophene ring and a nitrogen derivative thereof as constituent units, and a polymer having such a material as the side chain, showing that these NLO materials have a high $\beta\mu$ value and a thermal stability of 280° C. or above.

However, of the NLO materials disclosed in Japanese Patent Applications Laid-open KOKAI No. 6-157511 and No. 7-173116, a material having a high $\beta\mu$ value of $1,200 \times 10^{-48}$ esu or above (therefore expected to have a high $r_{33}$ value), as exemplified by a material having as the basic structure a structure wherein an aromatic ring is bonded to a thiophene ring substituted with a tricyanovinyl group —C(CN)=C(CN)$_2$, has a $\lambda_{max}$ of 500 nm or greater. Hence, the material has an optical transparency insufficient for controlling light of about 830 nm, having a problem of a large transmission loss.

The length of bond between the NLO material and the polymer greatly affects the $r_{33}$ value because the orientation efficiency changes with a change in the bond length. However, it is hitherto unknown what the optimum bond length is for the NLO materials of this type.

SUMMARY OF THE INVENTION

An object of the present invention is to provide a compound (embracing a polymer) capable of second higher harmonic generation (SHG), and electro-optic control of electromagnetic waves having a wavelength ranging between 300 nm and 2,000 nm, once oriented by a suitable method, a composition containing the compound, a nonlinear optical element and an optical device which are prepared using them, and a process for producing them.

To achieve the above object, the present invention employs a conjugated long compound having a vinylene group between an aromatic ring and a thiophene ring. With an elongation of conjugation length, the secondary nonlinear constant $\beta$ becomes greater, and hence the $\beta\mu$ value also becomes greater, but usually resulting in an increase in the $\lambda_{max}$. As stated previously, in order to decrease transmission loss of light in a waveguide, it is preferable to make the $\lambda_{max}$ as small as possible.

Accordingly, the present inventors made studies on various compounds, and as a result they have discovered that compounds 1a to 1i as shown below have a high $\beta\mu$ value of about $1,500 \times 10^{-48}$ esu and has no $\lambda_{max}$ of 500 nm or greater. Because of such a high $\beta\mu$ value and small $\lambda_{max}$, a waveguide making use of any of these compounds can attain a sufficient optical transparency and can enjoy a small transmission loss when, e.g., light of about 830 nm is transmitted. This is presumably due to the fact that a 1-position substituted dicyanovinyl group —C(—Ar$^2$—Y)=C(CN)$_2$ is used as an electron attractive group in place of the tricyanovinyl group.

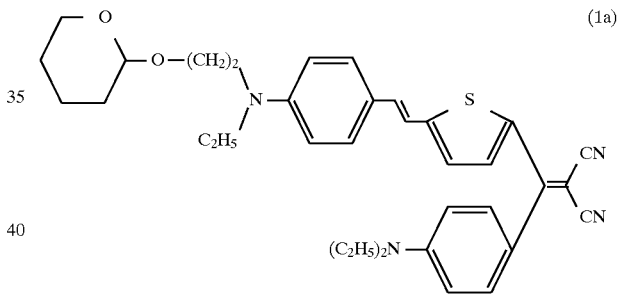

(1a)

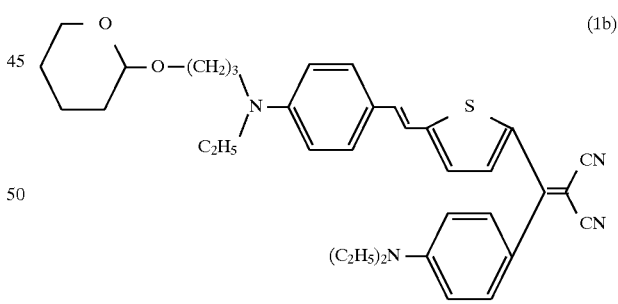

(1b)

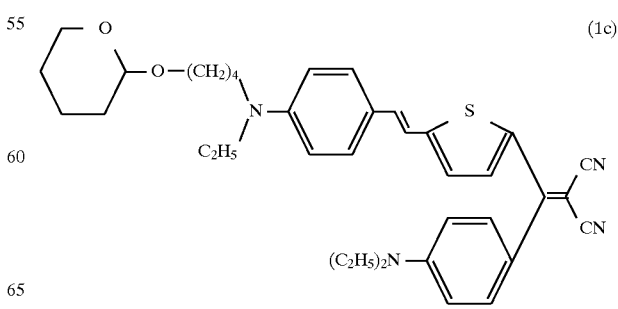

(1c)

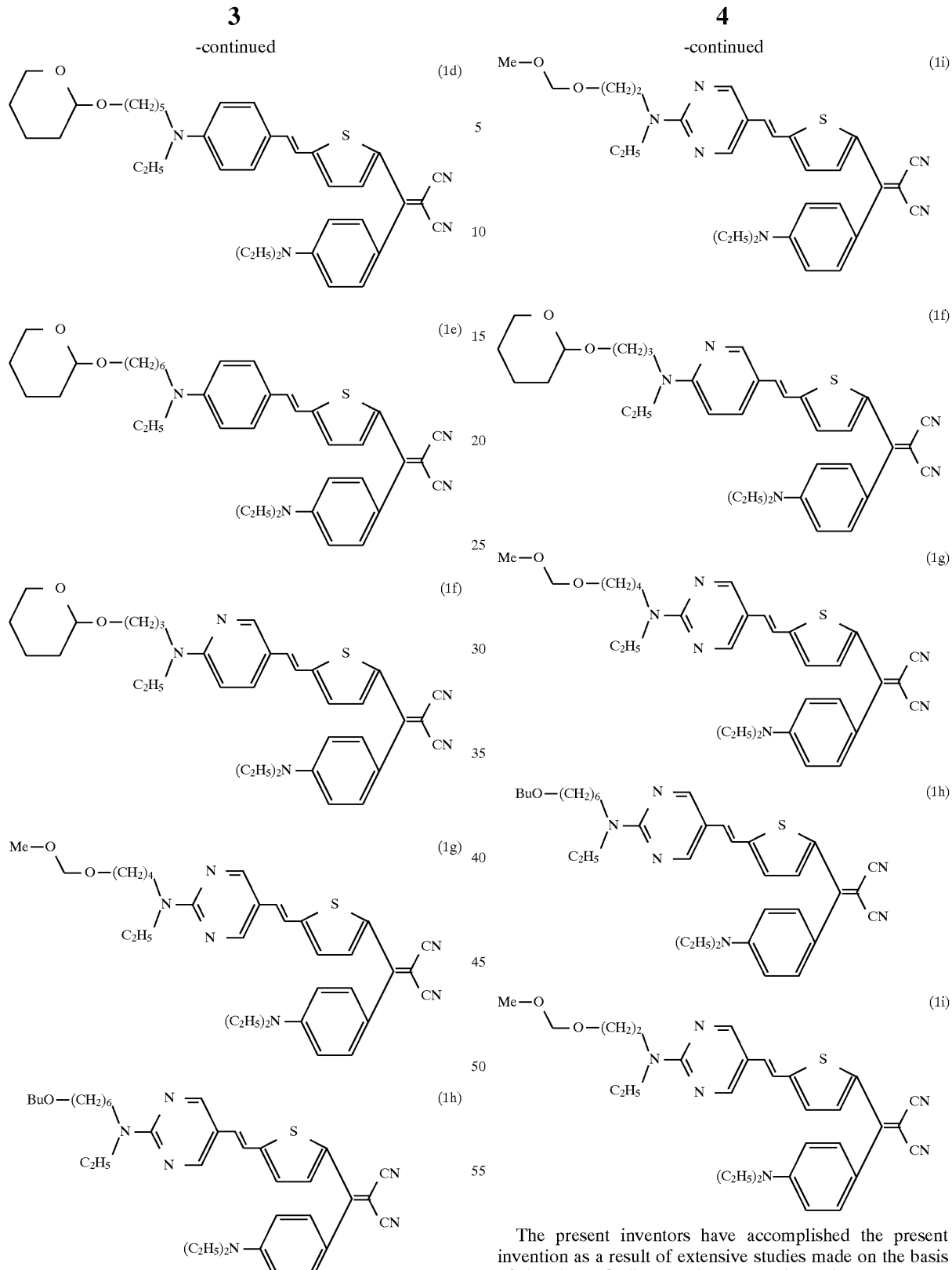
The present inventors have accomplished the present invention as a result of extensive studies made on the basis of the above finding. In the present invention, a structure wherein a thiophene ring substituted with a 1-position substituted dicyanovinyl group and an aromatic ring are bonded through a vinylene group is employed as the basic structure. This has made it possible to meet both the requirements usually conflicting with each other that the $\beta\mu$ value be great and the $\lambda_{max}$ be small.

As a heteroaromatic compound made functional so as to be used in nonlinear optical materials, the present invention provides a heteroaromatic compound represented by the following Formula (1), (2), (3) or (4).

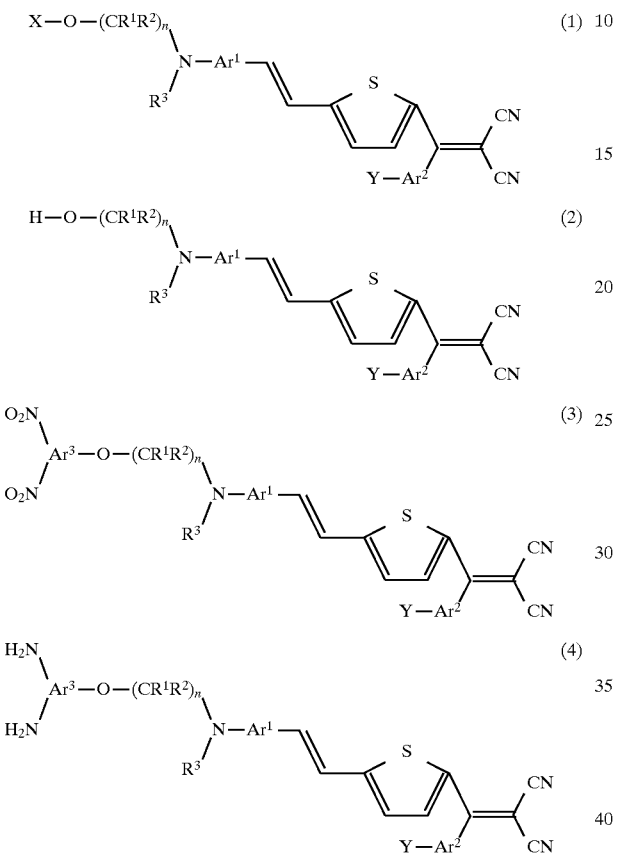

wherein $Ar^1$, $Ar^2$ and $Ar^3$ each independently represent an aromatic group or an aromatic group having a substituent, $R^1$, $R^2$ and $R^3$ each independently represent a hydrogen atom or a monovalent organic group, X represents a monovalent organic group, Y represents a hydrogen atom or a monovalent functional group, and n represents an integer of 2 to 10.

The present invention also provides an organic polymer having a first atomic group represented by the following Formula (5). Such an organic polymer includes, e.g., a polymethacrylate having this first atomic group on the side chain of its molecule, and a polyimide or polyimide precursor having this first atomic group on the side chain.

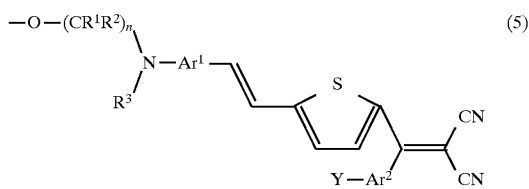

wherein $Ar^1$ and $Ar^2$ each independently represent an aromatic group or an aromatic group having a substituent, $R^1$, $R^2$ and $R^3$ each represent a hydrogen atom or a monovalent organic group, Y represents a hydrogen atom or a monovalent functional group, and n represents an integer of 2 to 10.

The organic polymer may further have a second atomic group represented by the following Formula (6). Such an organic polymer includes, e.g., a polyimide or polyimide precursor having this second atomic group as a diamine residual group.

wherein $Ar^3$ represents an aromatic group or an aromatic group having a substituent, and is bonded to the first atomic group.

The present invention also provides an organic polymer produced from a starting material containing the diamine represented by the above Formula (4). This organic polymer includes a polyimide precursor obtained by allowing the diamine to react with a carboxylic anhydride and a polyimide obtained by curing the precursor.

The present invention further provides a copolymer produced by mixing and heating a first polyimide precursor obtained by allowing the diamine to react with the carboxylic anhydride and a second polyimide precursor, and provides a polyimide copolymer obtained by curing the above copolymer.

The present invention still further provides a nonlinear optical element such as a core of an optial waveguide switch, obtained by curing a resin precursor composition of the present invention or comprised of a resin composition of the present invention, and an optical device having such an element.

The present invention still further provides a process for producing the above novel compound (embracing the polymer) and the compositions thereof, and a process for producing the nonlinear optical element and optical device making use of them.

BRIEF DESCRIPTION OF THE DRAWINGS

FIG. 2 is a flow chart showing a process for producing an optical device in Example 10.

FIGS. 3A and 3B are a $^1$H-NMR chart of a polyimide precursor obtained according to Synthesis Example 6(1).

FIGS. 4A and 4B are a $^1$H-NMR chart of a copolymer (dye density: 12.2%) obtained according to Synthesis Example 6(2).

DETAILED DESCRIPTION OF THE PREFERRED EMBODIMENT

Figure 1:
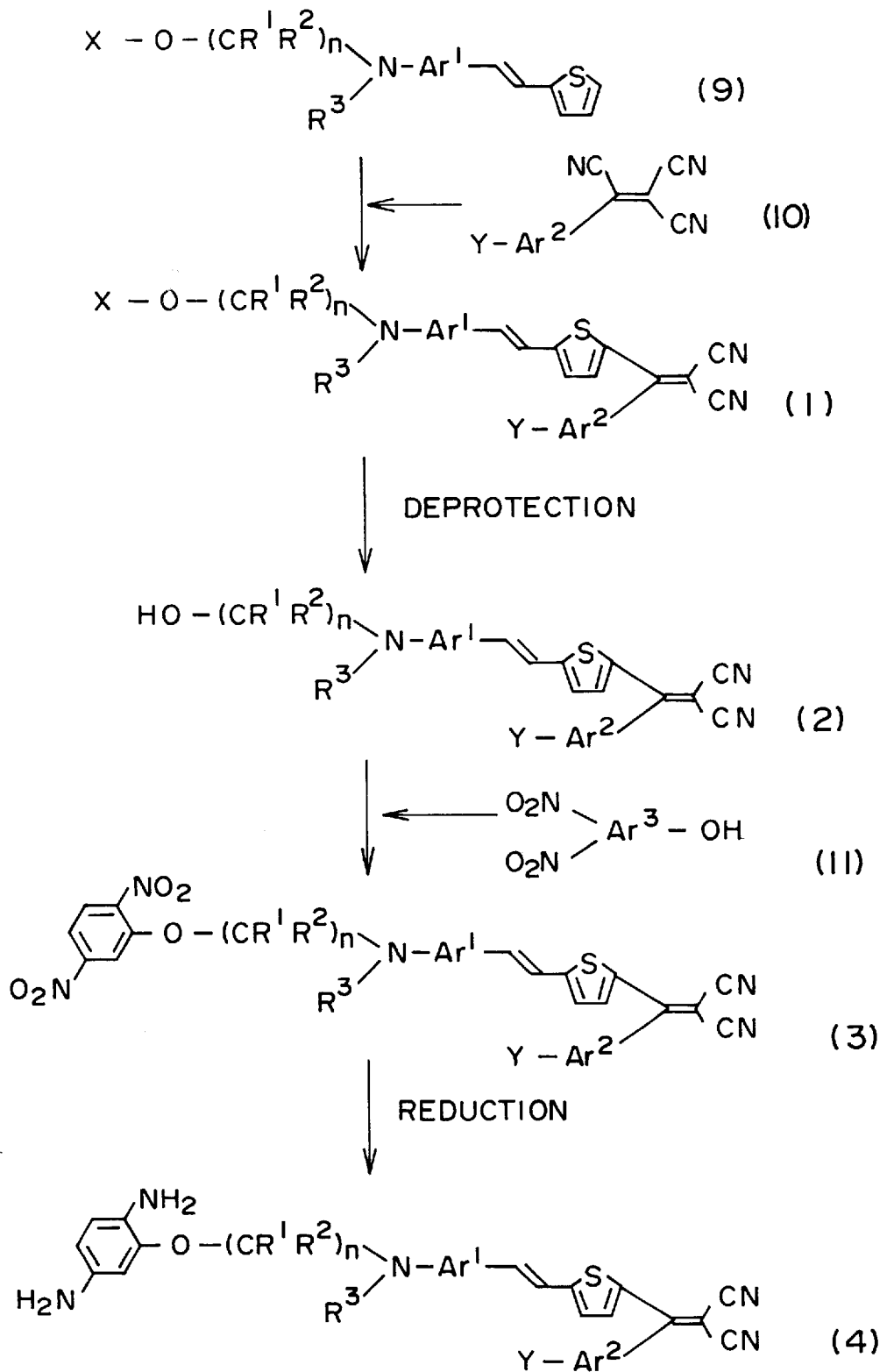
FIG. 1 is a schematic diagram showing a route of synthesizing the compound of the present invention, having nonlinear optical activities.

A route of synthesizing the heteroaromatic compound of the present invention is shown in FIG. 1.

The compound represented by the above Formula (1) (hereinafter called "compound 1") can be synthesized through a metalation step of treating a compound of Formula (9) with a metalation reagent and a condensation step of allowing the resulting metal compound to react with a compound of Formula (10).

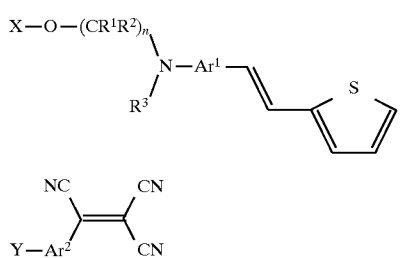

The groups Ar¹ and Ar² may include phenyl-diyl, naphthalene-diyl, biphenyl-diyl, thiophene-diyl, benzo[b]thiophene-diyl, naphtho[2,3-b]thiophene-diyl, thianthrene-diyl, furan-diyl, pyran-diyl, benzo[b]furan-diyl, isobenzofuran-diyl, chromene-diyl, xanthene-diyl, phenoxanthene-diyl, 2H-pyrrole-diyl, pyrrole-diyl, imidazole-diyl, pyrazole-diyl, pyridine-diyl, pyrazine-diyl, pyrimidine-diyl, pyridazine-diyl, indolizine-diyl, isoindole-diyl, 3H-indole-diyl, indole-diyl, 1H-indazole-diyl, purine-diyl, 4H-quinoline-diyl, isoquinoline-diyl, quinoline-diyl, phthalazine-diyl, naphthalidine-diyl, quinoxaline-diyl, quinazoline-diyl, cinnoline-diyl, pteridine-diyl, 4aH-carbazole-diyl, carbazole-diyl, β-carboline-diyl, phenanthridine-diyl, acrydine-diyl, perimidine-diyl, phenanthroline-diyl, phenazine-diyl, phenarsazine-diyl, isothiazole-diyl, phenothiazine-diyl, isoxazole-diyl, furazane-diyl, phenoxazine-diyl, isochroman-diyl, chroman-diyl, pyrrolidine-diyl, pyrroline-diyl, imidazolidine-diyl, imidazoline-diyl, pyrazolidine-diyl, pyrazoline-diyl, piperidine-diyl, piperazine-diyl, indoline-diyl, isoindoline-diyl, quinuclidine-diyl and morpholine-diyl; derivatives of these; and position isomers of these.

The groups $R^1$, $R^2$ and $R^3$ are each a hydrogen atom, and also may include saturated hydrocarbon groups such as methyl, ethyl, propyl, butyl and pentyl, saturated cyclic hydrocarbon groups such as cyclopentyl and cyclohexyl, unsaturated hydrocarbon groups such as vinyl, allyl, cyclopentenyl, cyclohexenyl, benzyl and triphenylmethyl, perfluoroalkyl groups such as trifluoromethyl, pentafluoroethyl and heptafluoropropyl, and isomeric groups of these.

The group Y may include hydrogen and electron donative groups such as alkylamino groups, dialkylamino groups, arylamino groups, diarylamino groups, alkylarylamino groups, alkyl groups, alkenyl groups, alkyl sulfide groups, aryl sulfide groups, alkyloxy groups, aryloxy groups, a hydroxyl group and a thiol group, as well as a nitro group, a nitroso group, alkynyl groups, acyl groups, a formyl group, aryl groups, alkyl sulfoxide groups, aryl sulfoxide groups, alkyl sulfone groups, aryl sulfone groups, and halogen atoms. These may each have a substituent.

As examples of the compound 1, it may include compounds 1a to 1i shown below.

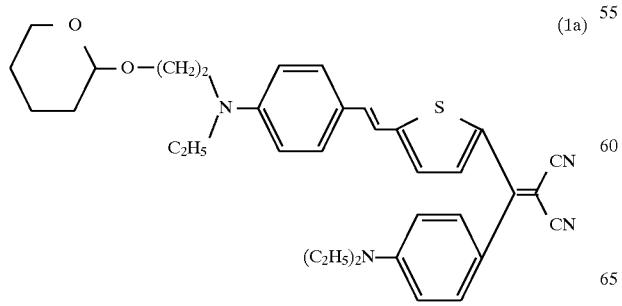

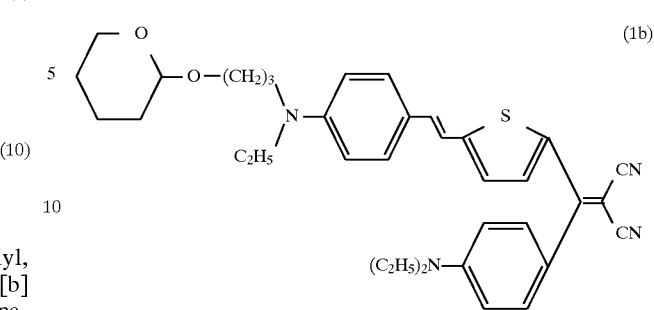

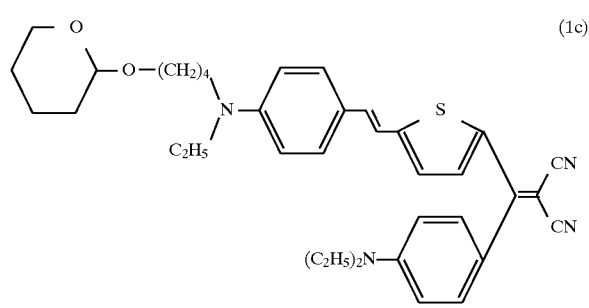

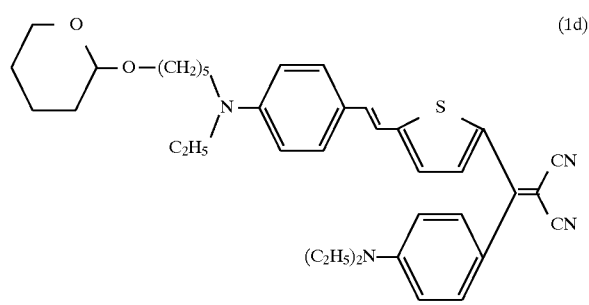

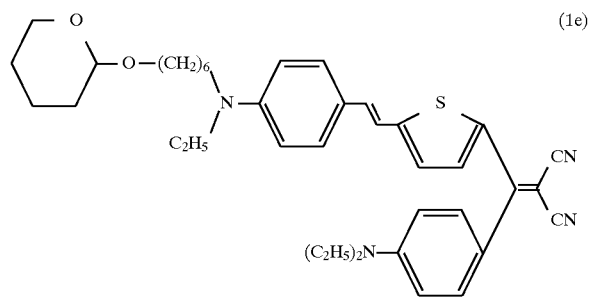

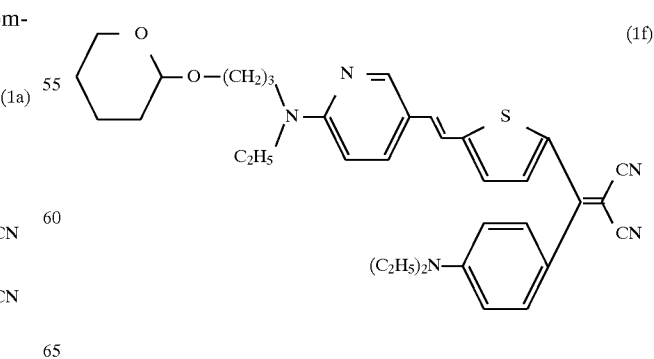

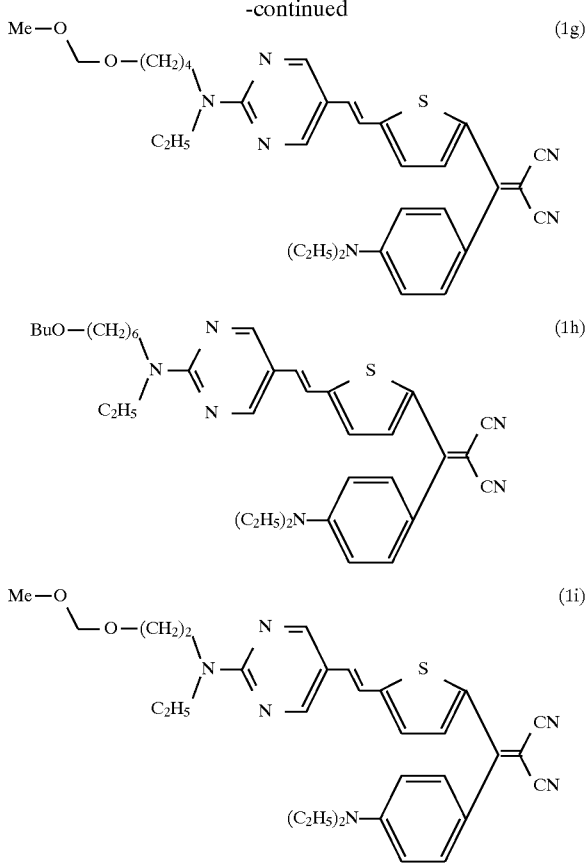

The metalation reagent mentioned above may include lithiation reagents such as methyllithium, butyllithium, t-butyllithium and phenyllithium, Grignard reagents such as methylmagnesium bromide, methylmagnesium chloride and phenylmagnesium chloride, and magnesition reagents such as dimethylmagnesium and diphenylmagnesium. As a solvent used in this reaction, it may include ethers such as diethyl ether, tetrahydrofuran and dioxane, alkanes such as pentane and hexane, aromatic solvents such as benzene, toluene and xylene, and mixtures of any of these. In the metalation step, the reaction may be carried out at a temperature of usually from −78° to 0° C., and preferably from −50° to −10° C. In the condensation step, in order to prevent decomposition of the metalation compound, the reaction may preferably be carried out at a low temperature of from −50° to −78° C., which is thereafter gradually raised to room temperature.

The compound 1 may be synthesized in this way and the group X may be eliminated, so that the compound represented by Formula (2) (hereinafter called "compound 2") can be obtained. When the compound 2 is obtained, the group X may preferably be a protective group. For example, it may preferably be an acetal group represented by the following Formula (12).

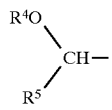

In the formula, $R^4$ and $R^5$ are each an organic group independently selected from, e.g., saturated hydrocarbon groups such as methyl, ethyl, propyl, butyl and pentyl, saturated cyclic hydrocarbon groups such as cyclopentyl and cyclohexyl, unsaturated hydrocarbon groups such as vinyl, allyl, cyclopentenyl, cyclohexenyl, benzyl and triphenylmethyl, perfluoroalkyl groups such as trifluoromethyl, pentafluoroethyl and heptafluoropropyl, aryl groups such as phenyl, p-methylphenyl, naphthyl, pyridinyl, pyrimidinyl and pyridazinyl, and isomeric groups of these. $R^4$ and $R^5$ may combine each other to form a ring. In such a case, the group X forms as a whole a heterocyclic ring containing an oxygen atom, such as a tetrahydrofuran-2-yl group and a tetrahydropyran-2-yl group.

Besides, the protective group used as the group X includes protective groups deprotectable under acidic conditions, such as a triphenylmethyl group, a trimethylsilyl group, a triphenylsilyl group and a diphenylmethylsilyl group, acyl groups deprotectable under base hydrolytic conditions, such as an acetyl group and a benzoyl group, and protective groups deprotectable with a Lewis acid, such as a methyl group and a triphenylmethyl group. In instances where it is not deprotected, organic groups of various types may be used as the group X, including alkyl groups having two or more carbon atoms such as ethyl, propyl and butyl, and aryl groups such as phenyl, p-tolyl, biphenyl, thienyl and pyridyl. The compounds 1a to 1g and 1i are examples in which the group X is the protective group.

In the case when the group X is the protective group, it is deprotectable with an acid. The acid used here may include mineral acids such as hydrochloric acid, nitric acid, phosphoric acid and boric acid, sulfonic acids such as methanesulfonic acid, p-toluenesulfonic acid and trifluoromethanesulfonic acid, and carboxylic acids such as formic acid, acetic acid and trifluoroacetic acid. As a solvent used in this instance, it may include water, alcohols such as methanol and ethanol, ethers such as diethyl ether, tetrahydrofuran and dioxane, aromatic solvents such as benzene, toluene and xylene, halogen type solvents such as dichloromethane and chloroform, and mixtures of any of these. When the acid is liquid, the acid itself may be used. There are no particular limitations on the reaction temperature. The reaction is accelerated under application of heat. As other reaction conditions, oxygen and light may preferably be shielded.

In the case when an acyl group deprotectable under base hydrolytic conditions is used as the group X, it is deprotected with a base. The base used here may include hydroxides such as sodium hydroxide, potassium hydroxide and barium hydroxide, metal alkoxides such as sodium methoxide and potassium tertiary butoxide, ammonia water, and metal amides such as sodium amide. As a solvent used in this instance, it may include water, alcohols such as methanol and ethanol, ethers such as diethyl ether, tetrahydrofuran and dioxane, aromatic solvents such as benzene, toluene and xylene, and mixtures of any of these. There are no particular limitations on the reaction temperature. The reaction is accelerated under application of heat. As other reaction conditions, oxygen and light may preferably be shielded.

In the case when the protective group deprotectable with a Lewis acid is used as the group X, it is deprotected with the Lewis acid. The Lewis acid used here may include aluminum chloride, ferrous chloride, ferric chloride, ferrous sulfate and ferric sulfate. As a solvent used in this instance, it may include halogen type solvents such as dichloromethane and chloroform. As reaction conditions, anhydrous conditions are necessary, and oxygen and light may preferably be shielded. There are no particular limitations on the reaction temperature. Side reaction is prohibited at a low temperature.

As examples of the compound 2, it may include compounds 2a to 2g shown below.

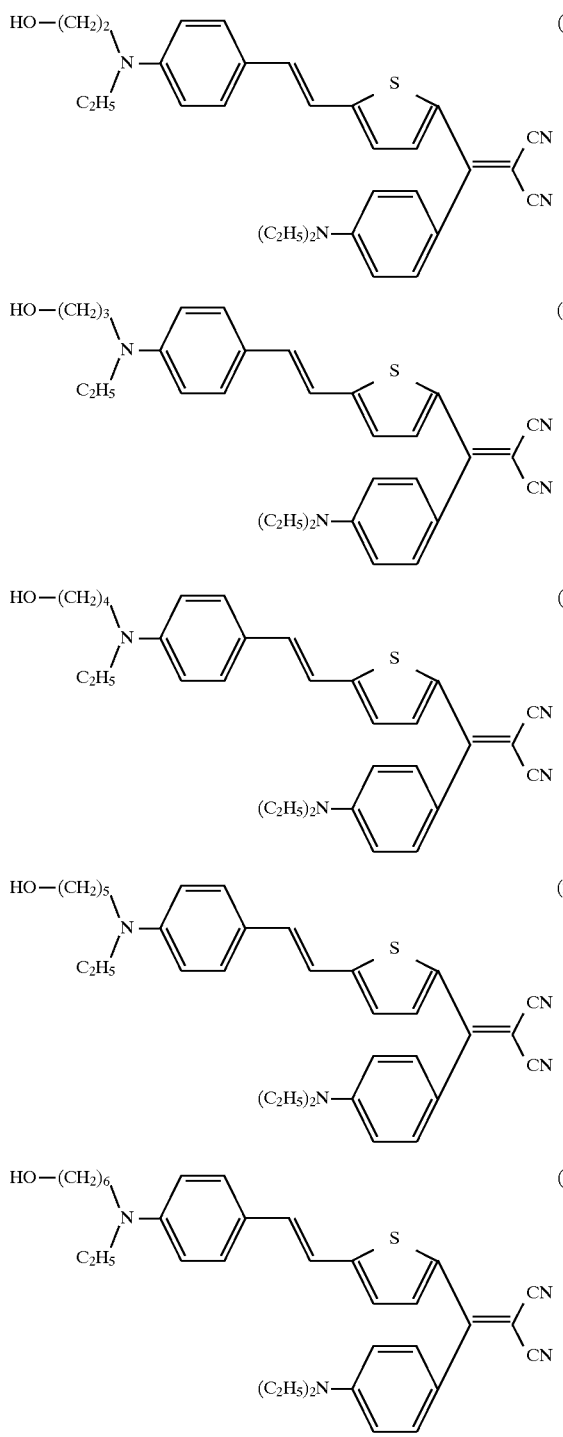

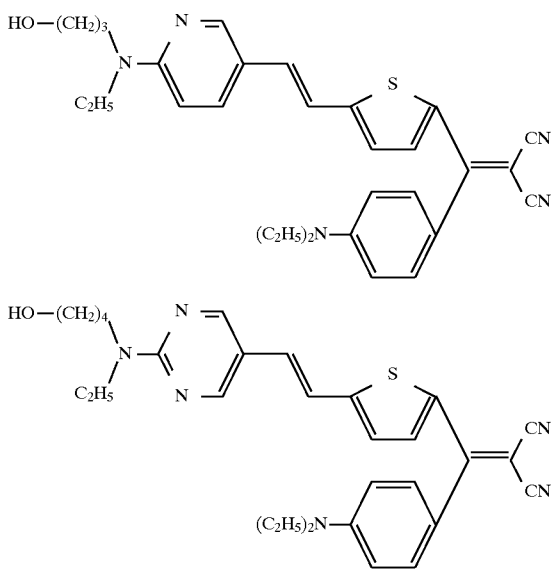

The compound of the present invention, e.g., the compound 2a has a $\beta\mu$ value of as great as $1,500\times10^{-48}$ esu. It has a $\lambda_{max}$ of 486 nm, and has 830 nm light transmission loss of as small as 4 dB/cm when it has a dye density of 20% by weight. Hence, these compounds are useful as materials used for optical waveguides and optical switches.

Condensation of the compound 2 with the compound represented by Formula (11) gives a dinitro compound represented by Formula (3) (hereinafter called "compound 3").

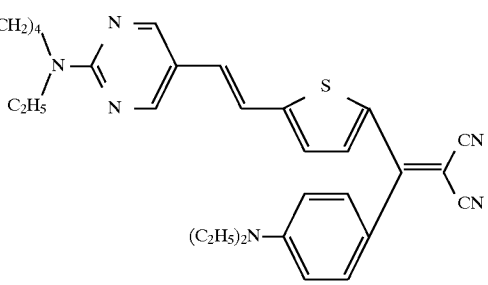

As a condensing reagent used in this condensation reaction, a triarylphosphine such as triphenylphosphine and a dialkyl azodicarboxylate such as diethyl azodicarboxylate are used in combination. As a solvent used in this condensation reaction, it may include ethers such as diethyl ether, tetrahydrofuran and dioxane, aromatic solvents such as benzene, toluene and xylene, halogen type solvents such as dichloromethane and chloroform, and mixtures of any of these. As reaction conditions, oxygen and light may preferably be shielded. There are no particular limitations on the reaction temperature. The reaction is accelerated under application of heat.

As examples of the compound 3, it may include compounds 3a to 3g shown below.

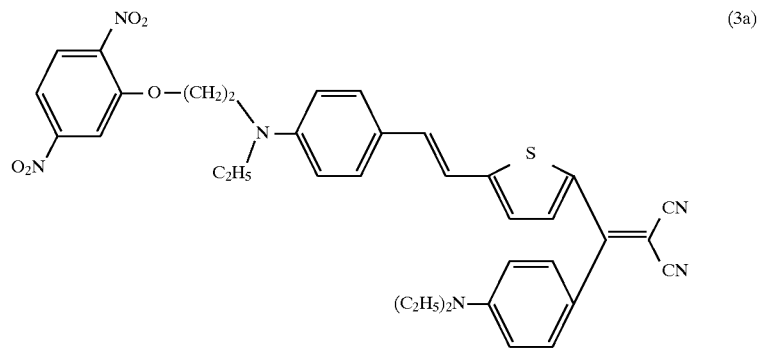
(3a)
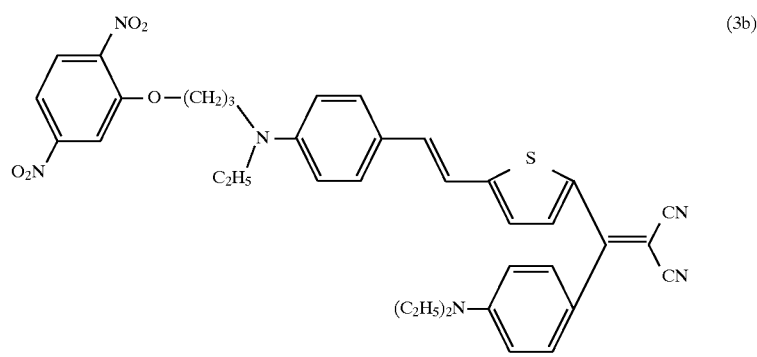
(3b)
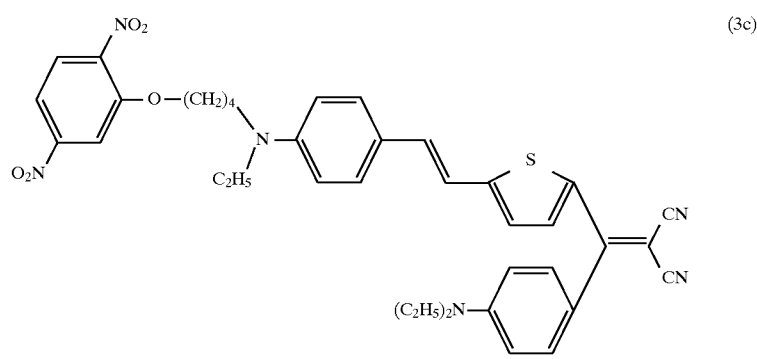
(3c)
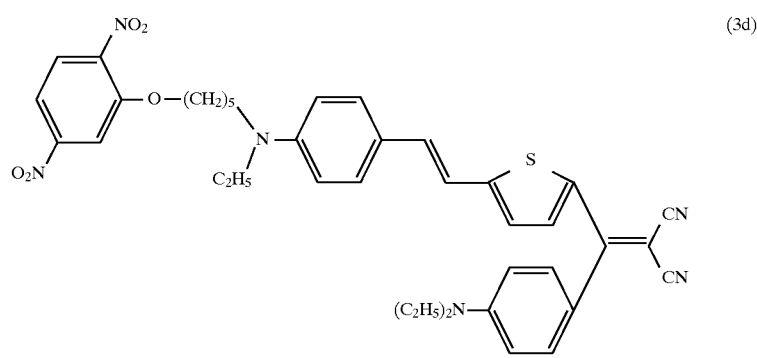
(3d)

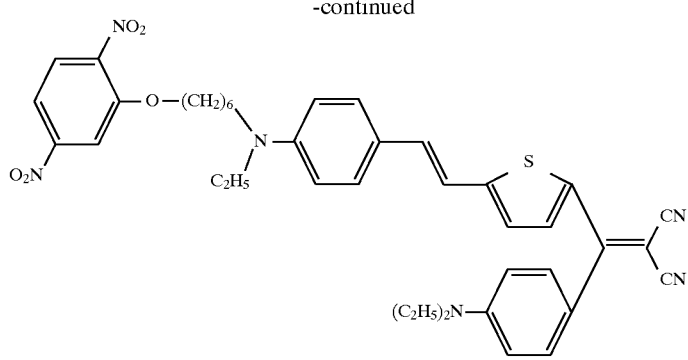

(3e)

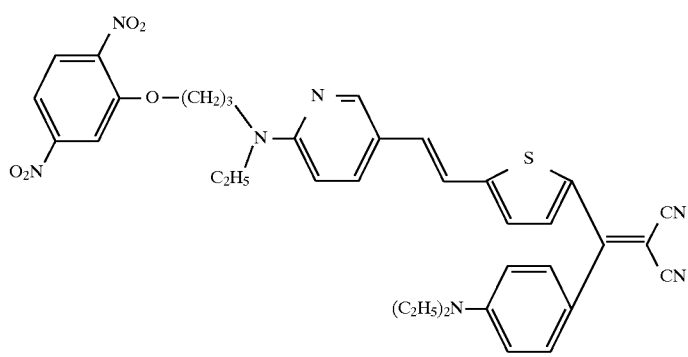

(3f)

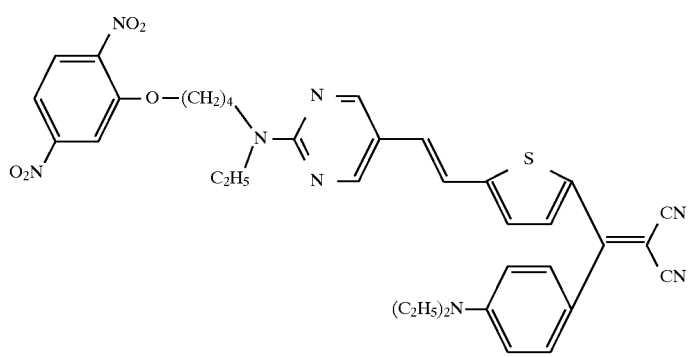

(3g)

Reduction of the compound 3 gives a diamine represented by Formula (4) (Compound 4).

As a reducing reagent used in this reduction reaction, stannous chloride, stannous chloride hydrate or the like is used. As a solvent used in this reaction, it may include water, hydrochloric acid, alcohols such as methanol and ethanol, ethers such as diethyl ether, tetrahydrofuran and dioxane, esters such as methyl acetate and ethyl acetate, aromatic solvents such as benzene, toluene and xylene, halogen type solvents such as dichloromethane and chloroform, and mixtures of any of these. Hydrochloric acid is preferred. In the case when hydrochloric acid is used as the solvent, the reaction mixture obtained after the reaction may preferably be neutralized with a base such as sodium carbonate, potassium carbonate, sodium hydroxide or potassium hydroxide so that the amino group formed is liberated to make the subsequent extraction easy. There are no particular limitations on the reaction temperature. The reaction is accelerated under application of heat in some cases. As other reaction conditions, oxygen and light may preferably be shielded.

As examples of the compound 4, it may include compounds 4a to 4g shown below.

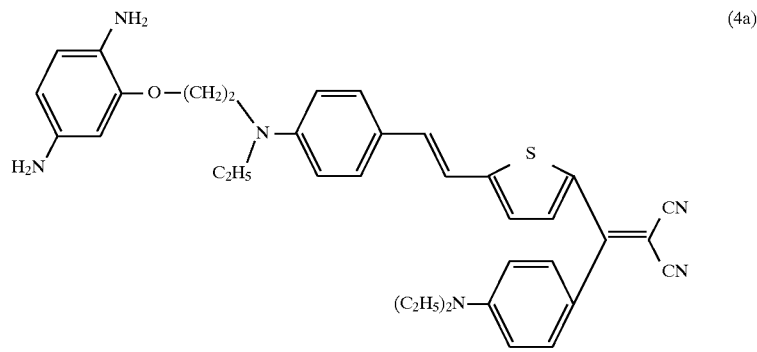
(4a)
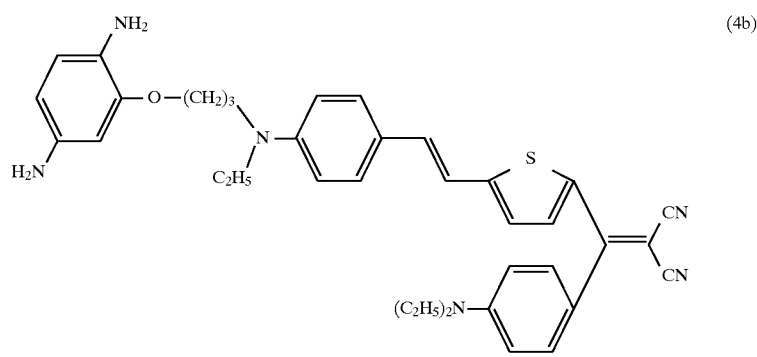
(4b)
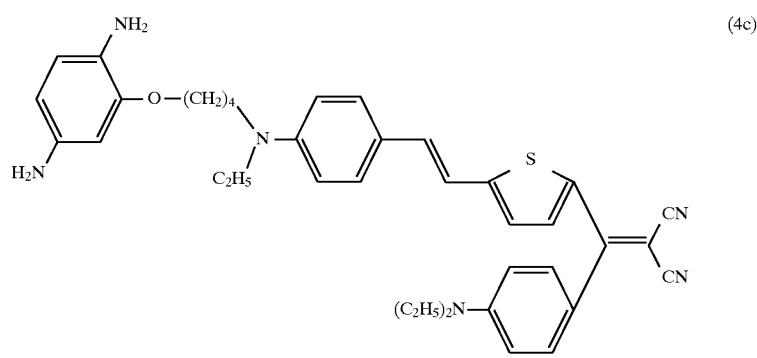
(4c)
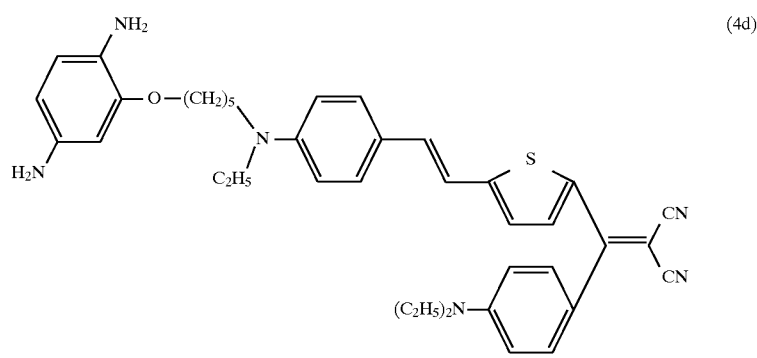
(4d)

-continued

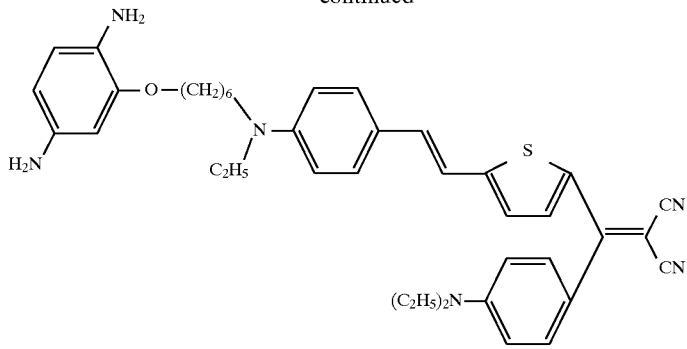

(4e)

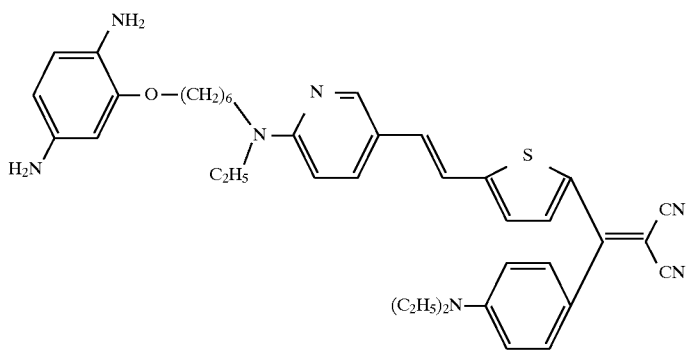

(4f)

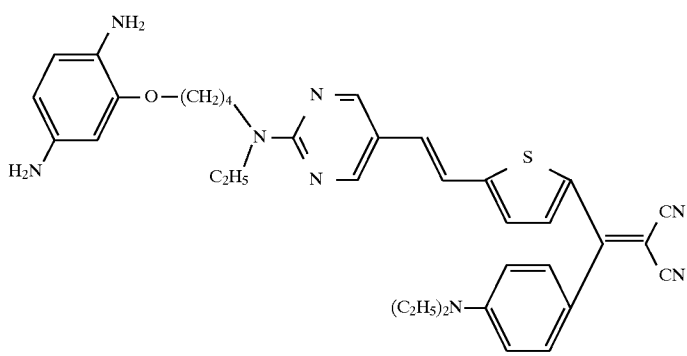

(4g)

The organic polymer provided in the present invention, which is produced from the starting material containing the compound 4, may include polyacrylates, polymethacrylates, polyacrylamides, polycarbonates, polysiloxanes, polyamides, polyimides, polyesters, polystyrene, polyether ketones, polyether ether ketones, polyphenyl ether ketones, and polyquinoline. As polyimide resins, they may include polyimide, polyamide-imide, polybenzimidazole, polyether imide, polyester imide, and polyisoimide. When put optical uses, those in which hydrogen atoms (preferably all the hydrogen atoms) have been substituted with fluorine or heavy hydrogen are preferred because of their small light transmission loss.

The above polymers can be produced by allowing the compound 4, an aromatic diamine, to react with a monomer or polymer precursor having a reactive functional group such as an epoxy group, a carboxylic acid group, a carboxylic anhydride group, a carboxylic halide group, a sulfonyl halide group, a phenolic hydroxyl group, an alkenyl group, a double-bond group, an acryloyl group, a methacryloyl group, an azide group, a chloromethyl group, an acetylene group, a cinnamic acid derivative group, a thiol group, a formyl group, an acetal group, an isocyanate group, a thioisocyanate group, a maleimide group, a cyano group, a halogen group, a hydroxyl group, an ester group, a cinnamilidene group, a diazo group, a dithiocarbamate group, a quinone group or a quinone dioxime group to combine them by covalent bonding, ionic bonding, coordinate bonding, hydrogen bonding or the like.

For example, the compound 4 diamine may be treated with a methacrylic acid halide in an organic solvent in the presence of a base to form it into an amide, whereby a bisacrylamide monomer can be synthesized in which the compound 4 is bonded through two amido groups. This monomer may be polymerized to thereby synthesize a poly(bismethacrylamide) having an atomic group represented by the following Formula (13).

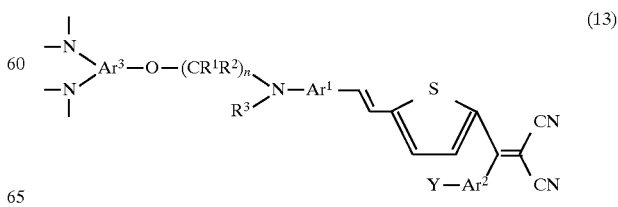

(13)

wherein $Ar^1$, $Ar^2$ and $Ar^3$ each independently represent an aromatic group or an aromatic group having a substituent, $R^1$, $R^2$ and $R^3$ each represent a hydrogen atom or a monovalent organic group, Y represents a hydrogen atom or a monovalent functional group, and n represents an integer of 2 to 10.

Using the compound 4 as an initiator, an epoxy compound may also be polymerized to thereby synthesize a pendant type epoxy resin having at its terminal the atomic group represented by the above Formula (13).

Besides the compound 4, the compounds 1 to 3 may be used to synthesize organic polymers. For example, since the compound 2 heterocyclic aromatic compound has a hydroxyl group, this may be esterified with a methacrylic acid halide in an organic solvent in the presence of a base, whereby a methacrylate monomer which is an ester of the compound 2 with methacrylic acid can be synthesized. This monomer may be polymerized to thereby synthesize a polymethacrylate having an atomic group represented by the following Formula (5).

phine and a dialkyl azodicarboxylate, to thereby synthesize a pendant type polymer having the atomic group represented by the above Formula (5).

The compound 4 is a diamine, and hence it may be allowed to react with a carboxylic anhydride to obtain a polyimide or a precursor thereof. Here, the polyimide precursor includes polyamic acids, polyamic acid halides, polyamic acid esterified products, and polyimide resins such as polyisoimides. The polyimide includes all products having different degrees of imidization, ranging from polyimide precursors to those completely imidized. In addition to such polyimides, it also includes polyamide-imides, polybenzimidazole, polyether imides, polyester imides, and polyisoimides. The polyimide precursor also includes polyamic acids, polyamic acid halides, polyamic acid esterified products, and polyimide resins such as polyisoimides.

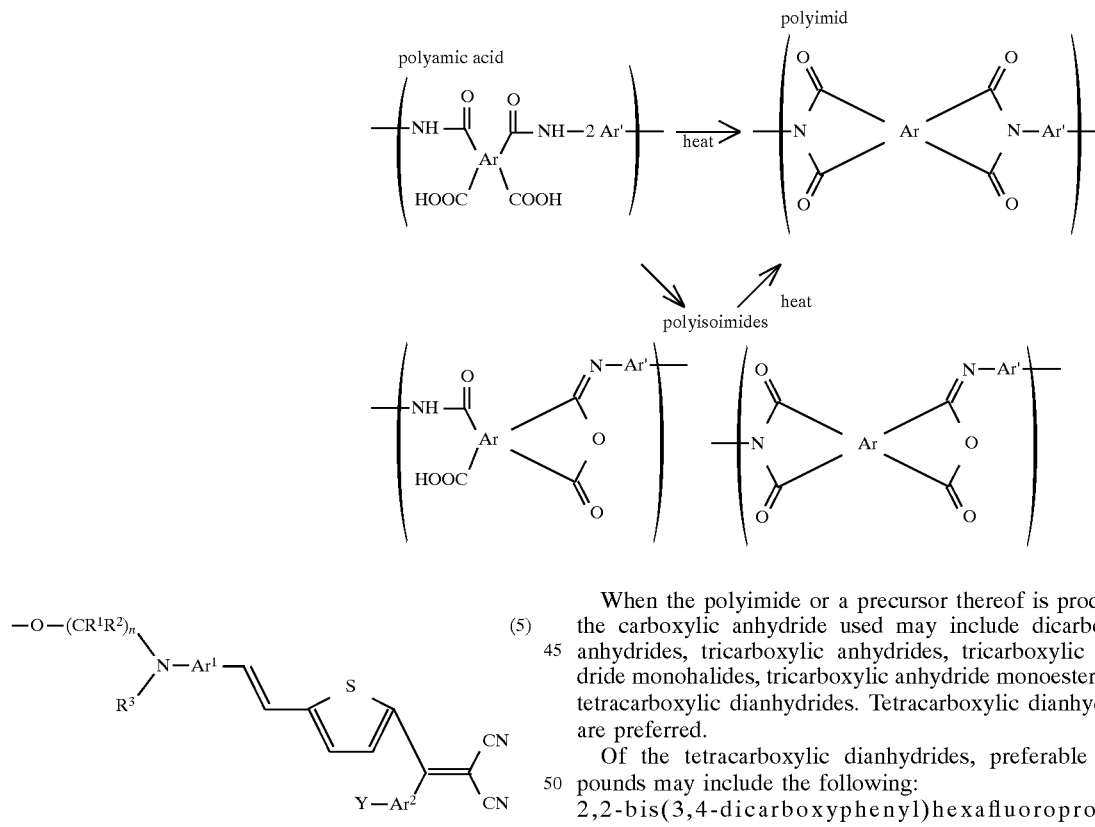

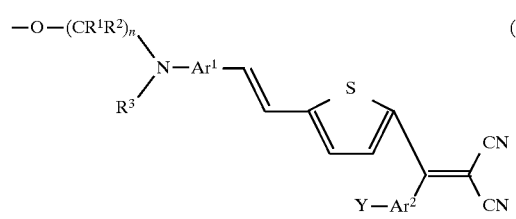

wherein $Ar^1$ and $Ar^2$ each independently represent an aromatic group or an aromatic group having a substituent, $R^1$, $R^2$ and $R^3$ each represent a hydrogen atom or a monovalent organic group, Y represents a hydrogen atom or a monovalent functional group, and n represents an integer of 2 to 10.

A polyimide having a phenolic hydroxyl group can be produced from, e.g., 4,4'-diamino-2,2'-dihydroxybiphenyl or 4,4'diamino-3,3'-dihydroxy-4,4'-biphenyl and a carboxylic dianhydride. Poly(4-acetyloxystyrene) may also be subjected to base hydrolysis to produce poly(4-hydroxystyrene). Accordingly, such a polymer having a phenolic hydroxyl group and the compound 2 may be subjected to ether-forming treatment using triphenylphos- When the polyimide or a precursor thereof is produced, the carboxylic anhydride used may include dicarboxylic anhydrides, tricarboxylic anhydrides, tricarboxylic anhydride monohalides, tricarboxylic anhydride monoesters, and tetracarboxylic dianhydrides. Tetracarboxylic dianhydrides are preferred.

Of the tetracarboxylic dianhydrides, preferable compounds may include the following:
2,2-bis(3,4-dicarboxyphenyl)hexafluoropropane dianhydride,
1,2,4,5-benzenetetracarboxylic dianhydride,
3-trifluoromethyl-1,2,4,5-benzenetetracarboxylic dianhydride,
3,6-bis(trifluoromethylmethyl)-1,2,4,5-benzenetetracarboxylic dianhydride,
3,6-difluoro-1,2,4,5-benzenetetracarboxylic dianhydride,
2,3,6,7-naphthalenetetracarboxylic dianhydride,
1,4,5,8-tetrafluoro-2,3,6,7-naphthalenetetracarboxylic dianhydride,
2,3,6,7-tetrafluoro-1,4,5,8-naphthalenetetracarboxylic dianhydride,
1,2,4,5-cyclohexanetetracarboxylic dianhydride,
1,2,3,4-cyclobutanetetracarboxylic dianhydride,
bis(3,4-dicarboxyphenyl) dianhydride,
bis(3,4-dicarboxyphenyl) ether dianhydride, bis(3,4-dicarboxyphenyl) sulfone dianhydride,
bis(3,4-dicarboxyphenyl) ketone dianhydride,
bis(3,4-dicarboxyphenyl)methane dianhydride,
bis[(3,4-dicarboxyphenyl)dimethylsilyl] ether dianhydride,
2,2-bis(3,4-dicarboxyphenyl)propane dianhydride,
2,2-bis(3,4-dicarboxyphenyl)-1,1,3,3-tetrafluoropropane dianhydride,
1,4-bis(3,4-dicarboxyphenyl)benzene dianhydride,
2,2-bis[4-(3,4-dicarboxyphenyloxy)phenyl]dodecane dianhydride,
2,2-bis[4-(3,4-dicarboxyphenyloxy)phenyl]tridecane dianhydride,
1,4-bis(3,4-dicarboxyphenyloxy)benzene dianhydride,
2,3,5,6-tetrafluoro-1,4-bis(3,4-dicarboxy-2,5,6-trifluorophenyloxy)benzene dianhydride,
bis(3,4-dicarboxy)cyclohexyl dianhydride,
bis(1,2-dicarboxyethyl) dianhydride, and
alkanediol bis(trimellitic anhydride). These carboxylic dianhydrides may be used in the form of a mixture of two or more kinds. In the alkanediol bis(trimellitic anhydride), the alkanes may preferably be those having 2 to 12 carbon atoms.

As examples of the tricarboxylic anhydrides, they may include trimellitic anhydrides and 4-hydroxycarbonylcyclohexanedicarboxylic anhydride. As examples of the tricarboxylic anhydride monohalides, they may include trimellitic anhydride chloride, trimellitic anhydride bromide and 4-chlorocarbonylcyclohexanedicarboxylic anhydride.

As examples of the tricarboxylic anhydride esterified products, they may include methyl trimellitate anhydride, ethyl trimellitate anhydride, propyl trimellitate anhydride, 4-methoxycarbonylcyclohexanedicarboxylic anhydride, and 4-ethoxycarbonylcyclohexanedicarboxylic anhydride.

When put to optical use, those in which hydrogen atoms (preferably all the hydrogen atoms) have been substituted with fluorine or heavy hydrogen are preferred because of their small light transmission loss. In particular, a compound represented by the following chemical formula (7) is preferred in view of optical characteristics.

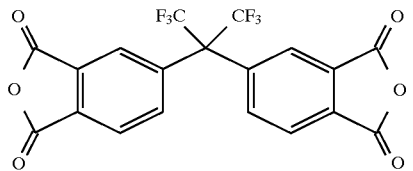

(7)

As solvents for the reaction to produce this polyimide or polyimide precursor, it is possible to use amide type solvents such as N,N-diemthylformamide, N,N-diemthylacetamide and N-methyl-2-pyrrolidinone, ether type solvents such as diethyl ether, tetrahydrofuran, dioxane and diglyme, aromatic solvents such as benzene, toluene and xylene, and mixtures of any of these. In particular, amide type solvents or ether type solvents are preferred.

The reaction to produce the polyimide precursor may preferably be carried out at a temperature of from 0° to 50° C. In order to make the polyimide or polyimide precursor thereof have a large molecular weight, a low temperature of from 0° to 50° C. is selected. In order to make it easy to cause the cleavage and recombination reaction of amide bonds, a temperature of 30° C. or above is selected. Accordingly, the reaction may be once carried out at a low temperature to make the molecular weight higher, and thereafter at a temperature of 30° C. or above to thereby control viscosity.

The imidization reaction may preferably be carried out at a temperature of 50° C. or above when carried out with heating. In order to complete the imidization, the temperature must be made higher than the glass transition point in some cases. It may also be carried out using a dehydrating reagent including trialkylsilyl halides such as trimethylsilyl chloride and triethylsilyl chloride, and N—N'-dialkyl carbodiimide such as N—N'-dicyclohexyl carbodiimide and N—N'-diisopropyl carbodiimide. In such a case, the reaction may preferably be carried out at a temperature of 50° C. or below.

The present invention further provides a copolymer produced by mixing and heating a first polyimide precursor obtained by allowing the compound 4 to react with the carboxylic anhydride and a second polyimide precursor, and provides a polyimide copolymer obtained by heating the above copolymer to cure. The polyimide copolymer can also be obtained by mixing and heating i) a first polyimide obtained by mixing and heating a first polyimide precursor obtained by allowing the compound 4 to react with the carboxylic anhydride and ii) a second polyimide obtained by heating a second polyimide precursor to cure.

As solvents used in the above mixing and heating treatment, it is possible to use amide type solvents such as N,N-dimethylformamide, N,N-dimethylacetamide and N-methyl-2-pyrrolidinone, ether type solvents such as diethyl ether, tetrahydrofuran, dioxane and diglyme, aromatic solvents such as benzene, toluene and xylene, and mixtures of any of these. In particular, amide type solvents or ether type solvents are preferred.

The cleavage and recombination reaction of amide bonds may readily take place when the above treatment is carried out at a temperature of 30° C. or above. Hence, the mixing and heating treatment makes polyimdes or precursors thereof having different constituent units present as equally as possible and makes the system uniform, and is useful for optimizing electro-optic characteristics and film forming properties.

As the second polyimide precursor, a polyimide precursor obtained by allowing the acid anhydride previously described to react with a diamine may be used. The diamine usable here may preferably include the following:
4,4'-diamino-2,2'-dimethylbiphenyl,
4,4'-diamino-2,2'-bis(trifluoromethyl)biphenyl,
4,4'-diamino-2,2'-difluorobiphenyl,
4,4'-diamino-3,3'-dimethylbiphenyl,
4,4'-diamino-3,3'-bis(trifluoromethyl)biphenyl,
4,4'-diamino-3,3'-difluorobiphenyl,
4,4'-diamino-2,2'-dihydroxybiphenyl,
4,4'-diamino-3,3'-dihydroxybiphenyl,
4,4'-diamino-2,2',3,3',5,5',6,6'-octafluorobiphenyl,
bis(4-diaminophenyl) ether,
bis(4-diaminophenyl) thioether,
bis(4-diaminophenyl) sulfone,
bis(4-diaminophenyl)methane,
bis(3-diaminophenyl) ether,
bis(3-diaminophenyl) thioether,
bis(3-diaminophenyl) sulfone,
bis(3-diaminophenyl) methane,
2,2-bis(4-diaminophenyl)propane,
2,2-bis(4-diaminophenyl)-1,1,1,3,3,3-hexafluoropropane,
2,2-bis(3-diaminophenyl)-1,1,1,3,3,3-hexafluoropropane,
2,2-bis[4-diaminophenyloxy)methyl]propane,
2,2-bis[4-(4-diaminophenyloxy)phenyl]propane,
2,2-bis[4-(3-diaminophenyloxy)phenyl]propane,
bis[1,2,5,6-tetrafluoro-4-(4-diaminophenyloxy)Phenyl] propane, 2,2-bis(4-diaminophenyloxy)phenyl-1,1,1,3,3,3-hexafluoropropane,
2,2-bis(3-diaminophenyloxy)phenyl-1,1,1,3,3,3-hexafluoropropane,
2,2-bis(4-diamino-2-trifluoromethylphenyloxy)phenyl-1,1,1,3,3,3-hexafluoropropane, alkalnediol [bis(4-aminopohenyl) ether], and
alkalnediol [bis(3-aminopohenyl) ether]. These diamines may be used in the form of a mixture of two or more kinds. The diamines may also be corresponding diisocyanates. In the alkanediols, the alkanes may preferably be those having 2 to 12 carbon atoms.

As a part of diamines, a silicon diamine may also be used. The silicon diamine includes 1,3-bis(3-aminopropyl)- 1,1,1-tetraphenyldisiloxane, 1,3-bis(3-aminopropyl)-1,1,1-tetramethyldisiloxane, and 1,3-bis(4-aminobutyl)-1,1,1-tetramethyldisiloxane.

When put to optical use, those in which hydrogen atoms (preferably all the hydrogen atoms) have been substituted with fluorine or heavy hydrogen are preferred because of their small light transmission loss.

When used as nonlinear optical materials, the polyimide copolymer of the present invention may;

(i) preferably have a refractive index difference of 0.02 or less between TE mode and TM mode, in order to retain optical characteristics of light signals transmitted for the purpose of light transmission;

(ii) preferably have a glass transition point (Tg) of 250° C. or above, in order to prevent deterioration of characteristics from being caused by processing heat when devices such as optical switches or photoelectric hybrid circuits are produced;

(iii) preferably have a light transmission loss of 1 dB/cm or less at wavelengths of from 0.7 to 1.6 μm used in light transmission; and (iv) preferably have a fluorine content of not more than 22.6% by weight, from the viewpoint of film forming properties and workability.

Accordingly, the second polyimide may preferably have;

(i) a refractive index difference of 0.02 or less between TE mode and TM mode;
(ii) a glass transition point (Tg) of 250° C. or above; and
(iii) have a light transmission loss of 1 dB/cm or less at wavelengths of from 0.7 to 1.6 μm; or (i) a refractive index difference of 0.02 or less between TE mode and TM mode;
(ii) a glass transition point (Tg) of 250° C. or above; and
(iv) a fluorine content of not more than 22.6% by weight.

It may more preferably have;
(i) a refractive index difference of 0.02 or less between TE mode and TM mode;
(ii) a glass transition point (Tg) of 250° C. or above;
(iii) a light transmission loss of 1 dB/cm or less at wavelengths of from 0.7 to 1.6 μm; and (iv) a fluorine content of not more than 22.6% by weight.

Accordingly, it is preferable to use as the second polyimide a precursor that fulfills these conditions. In particular, a precursor having a repeating unit represented by the following chemical formula (8) is preferred.

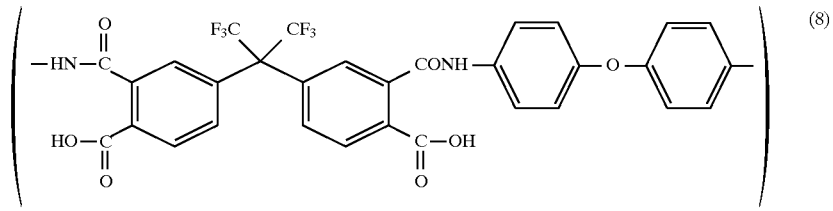

As described above, the compounds 1 to 4 can be used as raw materials of resin. Thus, the present invention provides a resin precursor composition containing any of the compounds 1 to 4. The present invention also provides a resin composition (or a resin precursor composition) containing at least one of the polymers (embracing copolymers) described above. The present invention further provides a resin composition containing at least one of the compounds 1 to 4 and the organic polymer. The resin composition (or a resin precursor composition) contains from 1 to 90 parts by weight (preferably from 10 to 30 parts by weight) of the organic polymer (or a resin precursor, a starting material) and from 10 to 99 parts by weight (preferably from 70 to 90 parts by weight) of the solvent. Assuming the total weight of the organic polymer and the solvent as 100 parts by weight, other components (e.g., a cross-linking agent, an initiator, a polymerization inhibitor and a plasticizer) may also be optionally contained in an amount of from 0 to 30 parts by weight.

As the organic polymer in the resin composition containing at least one of the compounds 1 to 4 and the organic polymer, various organic polymers may be used as organic polymers produced from starting materials containing the compound 4. When used in nonlinear optical materials, the organic polymer may include polyacrylates, polymethacrylates, polyacrylamides, polycarbonates, polysiloxanes, polyamides, polyimides, polyesters, polystyrene, polyether ketones, polyether ether ketones, polyphenyl ether ketones, and polyquinoline.

The resin composition (or a resin precursor composition) containing any of the compounds 1 to 4 includes a product prepared by dissolving or dispersing the compound in a solvent, a dried product thereof, a heat-treated product thereof, a reduced-pressure-treated product thereof, a pressure-treated product thereof, a light-irradiated product thereof, and a cured product thereof. The compounds 1 to 4 may be contained in any form, including all of the forms where the compound is chemically bonded, dissolved and dispersed, or non-dissolved and dispersed.

The form in which any of the compounds 1 to 4 is/are contained in the resin composition chiefly includes the following two forms.

(a) A form in which the compound 2 or compound 4 reacts with a monomer or polymer precursor having a reactive functional group, to effect covalent bond, ionic bond, coordinate bond or hydrogen bond to the polymer formed.

(b) A form in which any of the compounds 1 to 4 is/are dissolved or dispersed in the resin composition containing the polymer.

The resin composition having the above form (a) is produced by mixing the compound 2 or compound 4 with a monomer, monomer composition, polymer precursor composition or polymer precursor having a reactive functional group to allow the former to react with the latter to effect covalent bond, ionic bond, coordinate bond or hydrogen bond.

The resin composition having the above form (b) is produced by mixing any of the compounds 1 to 4 in a polymer or polymer composition, followed by dissolution or dispersion. The resin composition having the above form (b) can also be produced by mixing any of the compounds 1 to 4 in a monomer, monomer composition, polymer precursor or polymer precursor composition capable of forming a polymer, followed by dissolution or dispersion to produce a resin precursor composition, and polymerizing the composition.

EXAMPLES

I. Synthesis of Polyimide Precursor or Polyimide (n=2)

Synthesis Example 1: Synthesis of Compound 1a (1) Synthesis of N-acetyl-4-bromoaniline:

In an atmosphere of argon, 25 g (145.3 mmols) of 4-bromoaniline was dissolved in 50 ml of methanol, and the solution obtained was cooled to 0° C., and thereafter 27.4 ml (2.0-fold equivalent weight) of acetic anhydride was dropwise added thereto. Thereafter, the solution obtained was restored to room temperature, and stirred for 20 minutes. To the reaction solution obtained, 250 ml of water was added, and a white solid deposited was collected by filtration, which was then washed with water, followed by natural drying to obtain 30.8 g of N-acetyl-4-bromoaniline (yield: 99.1%; a while solid).

The results of analysis of the compound thus obtained are shown below. Unless particularly noted, the data of $^1$H-nuclear magnetic resonance (hereinafter "NMR") in the present specification are data of measurement made using $CDCl_3$ as a solvent and tetramethylsilane as an internal standard.

Melting point: 167.2°–168.6° C. Infrared absorption (hereinafter "IR") spectrum [ν ($cm^{-1}$)]: 3264, 1666, 1600, 1586, 1524, 1482, 1368, 1302, 1252, 1102, 1062, 1040, 1002, 968, 814, 734, 502, 398; $^1$H-NMR Spectrum [δ (ppm)]: 2.17(s, 3H), 7.37(brs, 1H), 7.41(s, 4H)

(2) Synthesis of N-ethyl-4-bromoaniline:

In a stream of argon, 5.76 g (1.3-fold equivalent weight) of lithium aluminum hydride was added to 50 ml of anhydrous tetrahydrofuran (hereinafter "THF"), and the mixture obtained was cooled to 0° C., and thereafter 25 g (116.8 mmols) of N-acetyl-4-bromoaniline dissolved in 125 ml of anhydrous THF was slowly dropwise added thereto, followed by heating and reflux for 2 hours. The reaction solution obtained was restored to room temperature, and slowly poured in ice water. Ethyl acetate was added, and the mixture obtained was stirred for a while, followed by suction filtration, and the filtrate obtained was washed with ethyl acetate. The washed solution and the filtrate were combined, and then extracted with ethyl acetate. The extract obtained was washed with water, which was thereafter dried with anhydrous magnesium sulfate and then concentrated. The residue thus obtained was distilled (155° C./0.4 Torr) to obtain 17.3 g of N-ethtyl-4-bromoaniline (yield: 74.3%; a colorless oily liquid).

The results of analysis of the compound thus obtained are shown below.

Boiling point: 155° C. (0.4 Torr); IR Spectrum [ν ($cm^{-1}$)]: 3404, 2968, 2876, 1594, 1492, 1382, 1312, 1280, 1250, 1174, 1144, 1070, 800; $^1$H-NMR Spectrum [δ (ppm)]: 1.22(t, 3H, J=7.1 Hz), 3.08(q, 4H, J=7.1 Hz), 3.57 (brs, 1 H), 6.44(d, 2 H, J=8.9 Hz), 7.22(d, 2 H, J=8.9 Hz)

(3) Synthesis of N-ethyl-N-(2-hydroxyethyl)-4-bromoaniline:

17.3 g (86.7 mmols) of N-ethyl-4-bromoaniline, 22.7 ml (1.5-fold equivalent weight) of N,N-diisopropylethylamine and 9.64 ml (1.5-fold equivalent weight) of 2-bromoethanol were mixed, and the mixture obtained was heated at 125° C. for 2 hours in an atmosphere of argon. Next, to the reaction solution obtained, 1.5 ml (0.1-fold equivalent weight) of diisopropylethylamine and 0.64 ml (0.1-fold equivalent weight) of 2-bromoethanol were added, and the mixture obtained was heated at 125° C. for 3 hours in an atmosphere of argon. Water was added to the reaction solution obtained, which was then extracted with ethyl acetate. The organic layer obtained was dried with anhydrous magnesium sulfate and then concentrated. The residue thus obtained was purified by silica gel column chromatography developing system (chloroform) to obtain 14.7 g of N-ethyl-N-(2-hydroxyethyl)- 4-bromoaniline (yield: 69.5%; a colorless oily liquid).

The results of analysis of the compound thus obtained are shown below.

Boiling point: 180° C. (0.4 Torr); IR Spectrum [ν ($cm^{-1}$)]: 3340, 2932, 2880, 1858, 1586, 1488, 1350, 1264, 1212, 1178, 1130, 1038, 906, 790, 728; $^1$H-NMR Spectrum [δ (ppm)]: 1.14(t, 3H, J=7.0 Hz), 1.76(brt, 1H, J=5.3 Hz), 3.48–3.34(m, 4H), 3.77(brq, 2H, J=5.3 Hz), 6.63(d, 2H, J=9.1 Hz), 7.28(d, 2H, J=9.1 Hz)

(4) Synthesis of N-ethyl-N-[2-(tetrahydropyran-2-yl) oxyethyl]-4-bromoaniline:

14.7 g (60.3 mmols) of N-ethyl-N-(2-hydroxyethyl)-4-bromoaniline, 90 ml of chloroform, 10.68 ml (2.0-fold equivalent weight) of 3,4-dihydro-2H-pyran and 0.76 g (0.05-fold equivalent weight) of pyridine p-toluenesulfonate were mixed, and the mixture obtained was heated at 70° C. for 1.5 hours in an atmosphere of argon. Thereafter, a saturated aqueous sodium hydrogencarbonate solution was added to the reaction solution obtained, which was then extracted with chloroform (200 ml×2). The organic layer thus formed was washed with a saturated aqueous sodium hydrogencarbonate solution, which was then dried with anhydrous magnesium sulfate and thereafter concentrated. The residue thus obtained was purified by silica gel column chromatography (developing system: chloroform) to obtain 18.90 g of N-ethyl-N-[2-(tetrahydropyran-2-yl)oxyethyl]-4-bromoaniline (yield: quantitative; a colorless oily liquid).

The results of analysis of the compound thus obtained are shown below. IR Spectrum [ν ($cm^{-1}$)]: 3400, 3088, 2928, 2208, 1598, 1514, 1478, 1404, 1344, 1270, 1188, 1118, 1074, 1024, 986, 792, 730, 654, 484; $^1$H-NMR Spectrum [δ (ppm)]: 1.14(t, 3H, J=7.0 Hz), 1.43–1.60(m, 4H), 1.60–1.90 (m, 2H), 3.38(q, 2H, J=7.0 Hz), 3.43–3.60(m, 4H), 3.78–3.90(m, 2H), 4.59(t, 1H, J=3.3 Hz), 6.57(d, 2H, J=9.1 Hz), 7.25(d, 2H, J=9.1 Hz)

(5) Synthesis of N-ethyl-N-[2-(tetrahydropyran-2-yl) oxyethyl]-4-formylaniline:

Water content in 45.1 g (0.14 mol) of N-ethyl-N-[2-(tetrahydropyran-2-yl)oxyethyl]-4-bromoaniline was removed by azeotropic distillation carried out twice with toluene, followed by dissolution in 390 ml of anhydrous THF in an atmosphere of argon. The solution obtained was cooled to −78° C., and 195 ml (2.2-fold equivalent weight) of t-butyllithium (1.55M, an n-pentane solution) was dropwise added thereto, followed by stirring for 45 minutes. To the resulting reaction solution, 23 ml of N,N- dimethylformamide (hereinafter "DMF") was added, and the mixture obtained was stirred at room temperature for 5 hours. Thereafter, 100 ml of water was added to the resulting solution, which was then extracted with chloroform (100 ml×3). The organic layer obtained was dried with anhydrous sodium sulfate and then concentrated under reduced pressure. The residue thus obtained was purified by silica gel column chromatography (developing system: hexane/ethyl acetate=2/1) to obtain 35.0 g of N-ethyl-N-[2-(tetrahydropyran-2-yl)oxyethyl]-4-formylaniline (yield: 92%).

The results of analysis of the compound thus obtained are shown below.

IR Spectrum [ν (cm$^{-1}$)]: 2928, 2732, 1656, 1590, 1552, 1524, 1434, 1398, 1348, 1312, 1270, 1232, 1122, 1064, 1026, 984, 900, 866, 808, 706, 666; $^1$H-NMR Spectrum [δ (ppm)]: 1.22(t, 3H, J=7.0 Hz), 1.53(m, 4H), 1.74(m, 2H), 3.53(m, 3H), 3.66(m, 3H), 3.83(m, 1H), 3.94(m, 1H), 4.59(t, 1H, J=7.6 Hz), 6.74(d, 2H, J=8.9 Hz), 7.70(d, 2H, J=8.9 Hz), 9.71(s, 1H)

(6) Synthesis of 2-{N-ethyl-N-[2-(tetrahydropyran-2-yl)oxyethyl]anilin-4-yl}vinylthiophene:

Water content in 12.0 g (43.3 mmols) of N-ethyl-N-[2-(tetrahydropyran-2-yl)oxyethyl]-4-formylaniline was removed by azeotropic distillation carried out twice with toluene, followed by addition of 10.6 g (1.05-fold equivalent weight) of 2-thienylmethyl diethoxyphosphate, and the atmosphere was replaced with argon. Thereafter, 220 ml of anhydrous THF was added, and the solution obtained was cooled to 0° C., and 5.3 g (1.1-fold equivalent weight) of potassium t-butoxide was further added thereto, followed by stirring at room temperature for 1.25 hours. The resulting reaction solution was concentrated, and the residue thus obtained was purified by silica gel column chromatography (developing system: hexane/ethyl acetate=4/1) to obtain 15.3 g of 2-{N-ethyl-N-[2-(tetrahydropyran-2-yl)oxyethyl]anilin-4-yl}vinylthiophene (yield: 99%).

The results of analysis of the compound thus obtained are shown below.

IR Spectrum [ν (cm$^{-1}$)]: 2928, 1598, 1508, 1454, 1394, 1366, 1348, 1260, 1240, 1178, 1118, 1060, 1032, 1018, 976, 950, 812, 682, 526; $^1$H-NMR Spectrum [δ (ppm)]: 1.18(t, 3H, J=7.0 Hz), 1.53(m, 4H), 1.73(m, 2H), 3.54(m, 6H), 3.87(m, 2H), 4.60(t, 1H, J=3.4 Hz), 6.68(d, 2H, J=8.9 Hz), 6.85(d, 1H, J=16.0 Hz), 7.01(m, 2H), 7.03(d, 1H, J=16.0 Hz), 7.10(m, 1H), 7.32(d, 2H, J=8.9Hz)

(7) Synthesis of N,N-diethyl-4-tricyanovinylaniline:

In an atmosphere of argon, 42.3 g (0.28 mol) of N,N-diethylaniline was dissolved in 570 ml of anhydrous DMF, and the solution obtained was cooled to 0° C., and then 46.3 g (1.25-fold equivalent weight) of tetracyanoethylene was added thereto. Then, the solution obtained was restored to room temperature, and stirred for 4.5 hours, which was thereafter poured in 1 liter of a saturated aqueous sodium hydrogencarbonate solution. The solid thus deposited was filtered to obtain a residue, and the residue was subjected to azeotropic distillation twice with 300 ml of toluene to remove the water content. Thereafter, 300 ml of ethyl acetate was added, and the atmosphere was replaced with argon, followed by heating at 80° C. for 1 hour to effect dissolution. To the mixture obtained, 800 ml of hexane was added with stirring, and the solution obtained was cooled to room temperature. The solid thus deposited was collected by filtration, and the residue obtained was vacuum-dried to obtain 51.7 g of N,N-diethyl-4-tricyanovinylaniline (yield: 74%).

The results of analysis of the compound thus obtained are shown below.

IR Spectrum [ν (cm$^{-1}$)]: 2976, 2204, 1600, 1474, 1454, 1422, 1346, 1304, 1278, 1218, 1192, 1160, 1096, 1068, 998, 886, 818, 720, 662, 494; $^1$H-NMR Spectrum [δ (ppm)]: 1.29(t, 6H, J=7.1 Hz), 3.54(q, 4H, J=7.1 Hz), 6.73(d, 2H, J=9.5 Hz), 8.06(d, 2H, J=9.5 Hz)

(8) Synthesis of compound 1a 13.6 g (38.1 mmols) of 2-{N-ethyl-N-[2-(tetrahydropyran-2-yl)oxyethyl]anilin-4-yl}vinylthiophene was subjected to azeotropic distillation twice with toluene to remove the water content. Thereafter, in an atmosphere of argon, 380 ml of anhydrous THF was added, and the solution obtained was cooled to −78° C., and 23.2 ml (10.1-fold equivalent weight) of t-butyllithium (1.66M, an n-hexane solution) was dropwise added thereto. The reaction solution obtained was stirred for 2 hours (first stirring), which was thereafter stirred for 4 hours while gradually raising the temperature to −20° C. (second stirring), and again cooled to −78° C. Next, to the reaction solution obtained, 9.5 g (1.0-fold equivalent weight) of N,N-diethyl-4-tricyanovinylaniline was added, and the mixture obtained was stirred at room temperature for 6 hours (third stirring). The resulting reaction solution was concentrated, and the residue thus obtained was purified by silica gel column chromatography (developing system: hexane/ethyl acetate=2/1) to obtain 19.8 g of compound 1a (yield: 89%).

The results of analysis of the compound 1a thus obtained are shown below.

IR Spectrum [ν (cm$^{-1}$)]: 3428, 2200, 1588, 1508, 1476, 1404, 1344, 1260, 1174, 1054, 1022, 950, 792, 518; $^1$H-NMR Spectrum [δ (ppm)]: 1.23(m, 9H), 1.53(m, 4H), 1.74(m, 2H), 3.47(m, 8H), 3.57(m, 2H), 3.86(m, 2H), 4.59(t, 1H, J=3.3 Hz), 6.66(m, 4H), 6.98(dd, 2H, J=4.6 Hz, 16.0 Hz), 7.05(d, 1H, J=4.1 Hz), 7.33(d, 2H, J=8.9 Hz), 7.43(d, 2H, J=8.9 Hz), 7.63(d, 1H, J=4.1 Hz)

Synthesis Example 2: Synthesis of compound 2a 19.7 g (33.9 mmols) of the compound 1a, 340 ml of ethanol and 1.29 g (0.2-fold equivalent weight) of p-toluenesulfonic acid monohydrate were mixed, and the mixture obtained was heated and refluxed for 6 hours in an atmosphere of argon. The resulting reaction solution was concentrated, and the residue thus obtained was purified by silica gel column chromatography (developing system: hexane/ethyl acetate=1/1) to obtain 16.3 g of compound 2a (yield: 97%).

The results of analysis of the compound 2a thus obtained are shown below.

IR Spectrum [ν (cm$^{-1}$)]: 3472, 2942, 2348, 2200, 1590, 1516, 1472, 1402, 1338, 1262, 1174, 1152, 1038, 950, 796; $^1$H-NMR Spectrum [δ (ppm)]: 1.22(m, 9H), 3.48(m, 8H), 3.82(q, 2H, J=6.0 Hz), 6.65(d, 2H, J=9.0 Hz), 6.72(d, 2H, J=8.9 Hz), 6.96(d, 1H, J=16.0 Hz), 7.01(d, 1H, J=16.0 Hz), 7.03(d, 1H, J=4.1 Hz), 7.35(d, 2H, J=8.9 Hz), 7.43(d, 2H, J=9.0 Hz), 7.63(d, 1H, J4.2 Hz)

Synthesis Example 3: Synthesis of compound 3a 16.0 g (33.2 mmols) of the compound 2a was subjected to azeotropic distillation twice with toluene to remove the water content. Thereafter, 11.0 g (1.3-fold equivalent weight) of triphenylphosphine and 6.0 g (1.0-fold equivalent weight) of 2,5dinitrophenol were added, and 515 ml of anhydrous THF was further added in an atmosphere of argon, followed by stirring at room temperature for 40 minutes. Next, to the reaction solution obtained, a solution prepared by dissolving 6.6 ml (1.3-fold equivalent weight) of diethylazodicarboxylic acid diester in 20 ml of anhydrous THF was dropwise added. After stirring for 1 hour, the resulting reaction solution was concentrated, and the residue thus obtained was purified by silica gel column chromatography (developing system: chloroform/ethyl acetate=30/1) to obtain 20.8 g of compound 3a (yield: 97%).

The results of analysis of the compound 3a thus obtained are shown below.

IR Spectrum [ν (cm$^{-1}$)]2964, 2208, 1594, 1524, 1476, 1420, 1344, 1260, 1180, 1146, 1070, 802 $^1$H-NMR Spectrum [δ (ppm)]: 1.23(m, 9H), 3.44(q, 4H, J=7.1 Hz), 3.54(q, 2H, J=7.0 Hz), 3.87(t, 2H, J=5.2 Hz), 4.38(t, 2H, J=5.2 Hz), 6.67(d, 2H, J=9.0 Hz), 6.70(d, 2H, J=8.7 Hz), 6.99(s, 2H), 7.03(d, 1H, J=4.1 Hz), 7.37(d, 2H, J=8.7 Hz), 7.44(d, 2H, J=9.0 Hz), 7.63(d, 1H, J=4.1 Hz), 7.90(m, 2H)

Synthesis Example 4: Synthesis of compound 4a

To 20.8 g (31.3 mmols) of the compound 3a, 670 ml of concentrated hydrochloric acid was added, and the mixture obtained was stirred for 45 hours, followed by addition of 141 g (20-fold equivalent weight) of tin dichloride dihydrate. Next, the reaction solution obtained was stirred at room temperature for 2.5 days, and thereafter poured in 500 ml of ice water. The deposit formed was collected by filtration, and dissolved in water and chloroform. The solution obtained was neutralized (pH=9) with an aqueous potassium carbonate solution, followed by extraction with chloroform. The organic layer obtained was dried with anhydrous sodium sulfate, and thereafter concentrated. The residue thus obtained was purified by silica gel column chromatography (developing system: chloroform/ethyl acetate=7/3; light-shielded). The purified product thus obtained was dissolved in 85 ml of ethyl acetate, and the resulting solution was dropwise added in 1 liter of distilled hexane. The solid thus deposited was collected by filtration, and dried by heating under vacuum (70° C./1 mmHg, for 9 hours) to obtain 13.2 g of compound 4a (yield: 70%).

The results of analysis of the compound 4a thus obtained are shown below.

IR Spectrum [ν (cm$^{-1}$)]: 2932, 2200, 1590, 1508, 1470, 1404, 1344, 1272, 1176, 1144, 1048, 950, 798; $^1$H-NMR Spectrum [δ (ppm)]: 1.21(m, 9H), 3.33(brs, 4H), 3.45(m, 6H), 3.79(t, 2H, J=5.9 Hz), 4.11(t, 2H, J=5.9 Hz), 6.20(dd, 1H, J=2.2 Hz, 7.8 Hz), 6.22(d, 1H, J=2.2Hz), 6.56(d, 1H, J=7.8 Hz), 6.67(d, 2H, J=9.0 Hz), 6.74(d, 2H, J=8.8 Hz), 6.97(d, 1H, J=16.2 Hz), 7.01(d, 1H, J=16.2 Hz), 7.03(d, 1H, J=4.1 Hz), 7.33(d, 2H, J=8.8 Hz), 7.43(d, 2H, J=9.0 Hz), 7.64(d, 1H, J=4.1 Hz)

Synthesis Example 5: Synthesis of polyimide precursor

In a stream of nitrogen, 0.9 g (1.49 mmol) of the compound 4a was dissolved in 9.45 ml of diglyme. To the solution obtained, 0.66 g (1.0-fold equivalent weight) of 2,2-bis(3,4-dicarboxyphenyl)hexafluoropropane dianhydride was added at 0° C., followed by stirring for 2 hours. Next, the reaction solution obtained was stirred at room temperature for 4 hours to obtain 11.0 g of a polyimide precursor solution (solid content: 15% by weight).

The molecular weight of the polyimide precursor thus obtained was measured to find that the number average molecular weight (hereinafter "MN") was 5.87×105, weight average molecular weight (hereinafter "MW") was 1.67× 10$^6$, and degree of dispersion (MW/MN) was 2.83, each in terms of polystyrene (elution time: 22.654 minutes).

In the present specification, unless particularly noted, the values indicated as molecular weight are those obtained as values in terms of polystyrene, using gel permeation chromatography (hereinafter "GPC") (chromatopack: "Shimadzu C-R4A", available from Shimadzu Corporation; columns: "TOSOH, TSK-GEL, G2000HXL", available from Tosoh Co., Ltd.; developing system: DMF).

Synthesis Example 6: Synthesis of polyimide precursor copolymer (dye density: 12.2%)

(1) Synthesis of polyimide precursor:

In an atmosphere of nitrogen, 103.40 g (0.23 mol) of 2,2bis(3,4-dicarboxyphenyl)-1,1,1,3,3,3-hexafluoropropane dianhydride and 46.60 g (0.23 mol) of bis(4-diaminodiphenyl) ether were mixed with 850 g of N,N-dimethylacetamide. The mixture obtained was stirred at room temperature for 6 hours to obtain a polyimide precursor solution (solid content: 15% by weight). This solution had a viscosity of about 80 poises. The molecular weight of the polyimide precursor thus obtained was measured to find that MN was 1.30×10$^6$, MW was 4.51×10$^6$, and MW/MN was 3.48 in terms of polystyrene (elution time: 21.011 minutes).

A small amount of this copolymer was dropwise added to water, and the solid deposited was collected by filtration, followed by drying under reduced pressure. $^1$H-NMR spectra measured using deuterated dimethyl sulfoxide (DMSO-d$_6$) are shown in FIGS. 3A and 3B.

The polyimide precursor solution thus obtained was spin-coated on a silicon wafer of 5 inches diameter, having a surface formed of a silicon oxide layer, and the coating formed was heated to cure in an atmosphere of nitrogen, at 70° C. for 2 hours, subsequently at 160° C. for 30 minutes and further at 350° C. for 1 hour to form a polyimide film. As a result, the polyimide film thus obtained had a glass transition point (Tg) of 298° C. It also had a refractive index at 130 nm, of 1.5593 in TM mode and 1.5672 in TE mode, and a Δn of 0.0079. The light transmission loss was 0.52 dB in TM mode and 0.45 dB/cm in TE mode.

(2) Synthesis of copolymer:

10.4 g of the polyimide precursor solution obtained in Synthesis Example 5 and 30.8 g of the polyimide precursor solution obtained in the above (1) were mixed. The mixture obtained was stirred at room temperature for 2 hours, and then stirred at 65° C. for 2 hours and 15 minutes. The mixture thus obtained was pressure-filtered using a filter (pore diameter: 0.22 μm) to obtain 38.0 g of a copolymer polyimide precursor solution (solid content: 15% by weight) having a dye density of 12.2%. Here, the proportion (%) of the weight of atomic groups, obtained by excluding oxygen atom content from the atomic groups of the compound of Formula (5), to the weight of the polymer, is regarded as dye density.

The molecular weight of the copolymer thus obtained was measured to find that MN was 1.09×10$^6$ and MW was 3.57×10$^6$ in terms of polystyrene (elution time: 21.379 minutes; MW/MN: 3.27).

Figure 4A:
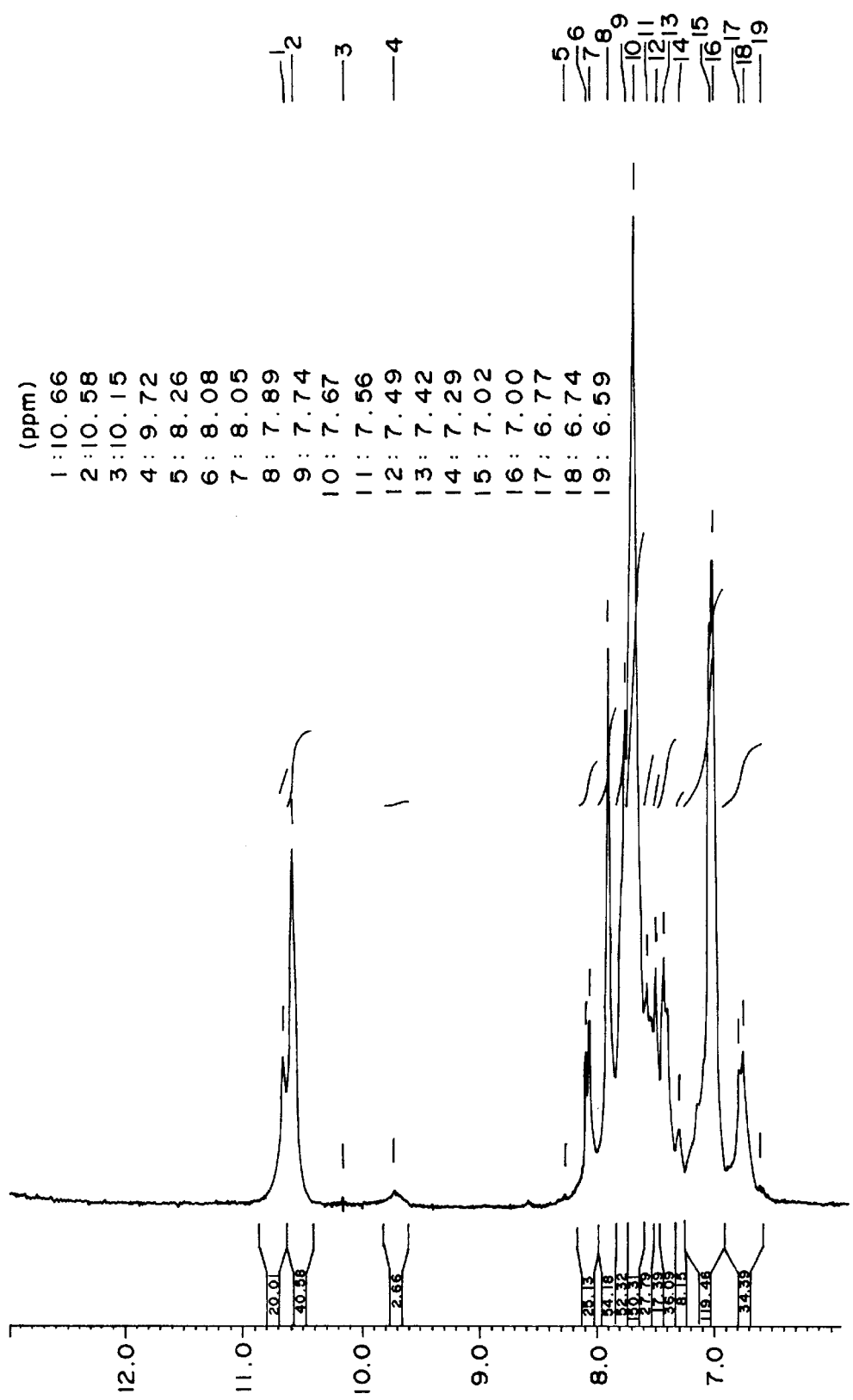

A small amount of this copolymer was dropwise added to water, and the solid deposited was collected by filtration, followed by drying under reduced pressure. $^1$H-NMR spectra measured using deuterated dimethyl sulfoxide (DMSO-d$_6$) are shown in FIGS. 4A and 4B.

Synthesis Example 7: Synthesis of polyimide precursor copolymer (dye density: 20.0%)

19.7 g of the polyimide precursor of Synthesis Example 5 and 27.6 g of a polyimide precursor solution obtained in the same manner as in Synthesis Example 6(1) were mixed. The mixture obtained was stirred at room temperature for 1.9 hours, and then stirred at 65° C. for 2 hours and 10 minutes. The mixture thus obtained was pressure-filtered using a filter (pore diameter: 0.22 μm) to obtain 43.5 g of a copolymer polyimide precursor solution having a dye density of 20.0%.

The molecular weight of the copolymer thus obtained was measured to find that MN was 9.82×10$^5$ and MW was 3.07×10$^6$ in terms of polystyrene (elution time: 21.625 minutes; MW/MN: 3.17).

Figure 5A:
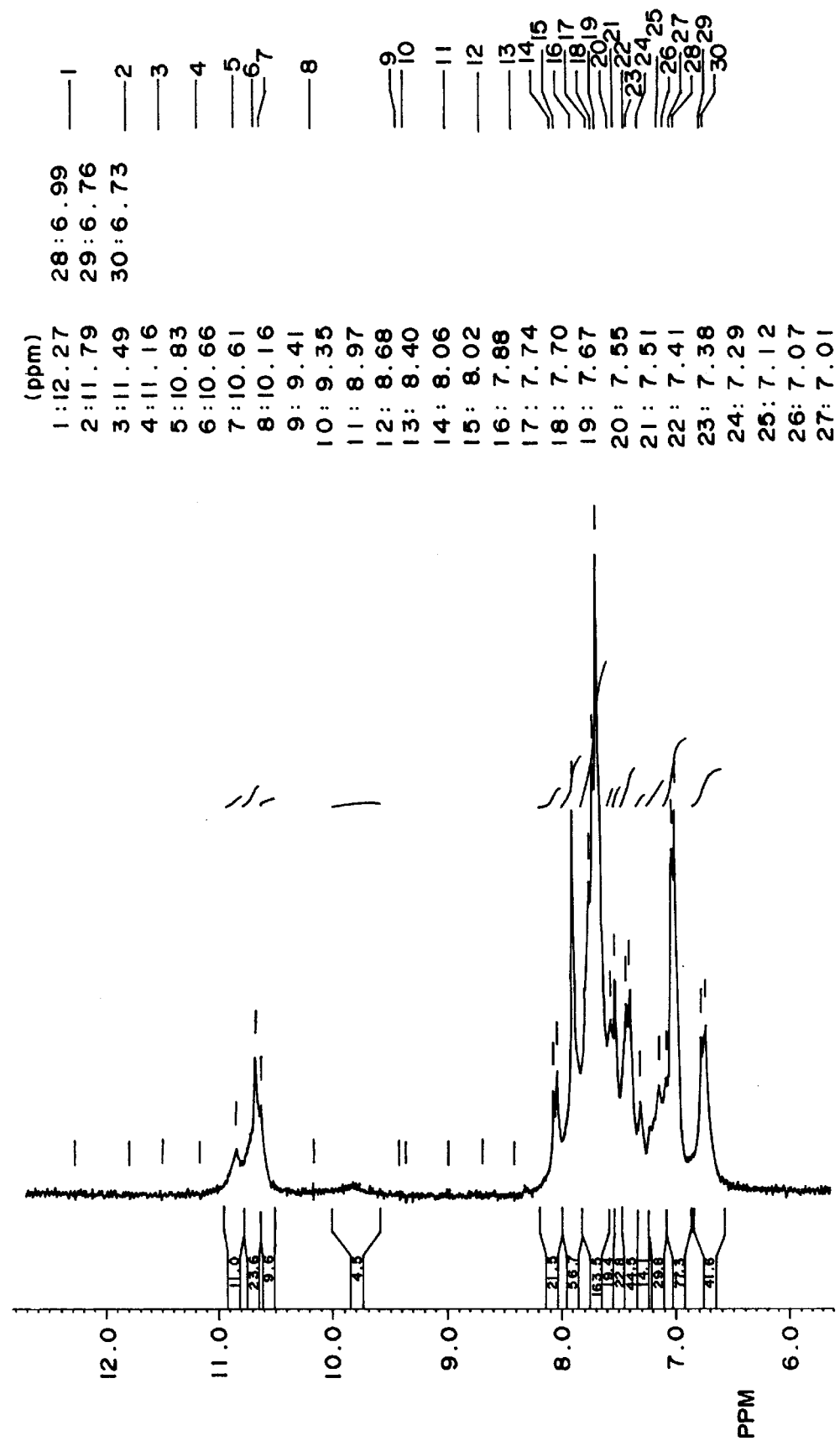
FIGS. 5A and 5B are a $^1$H-NMR chart of a copolymer (dye density: 20.0%) obtained according to Synthesis Example 7.
Figure 5B:
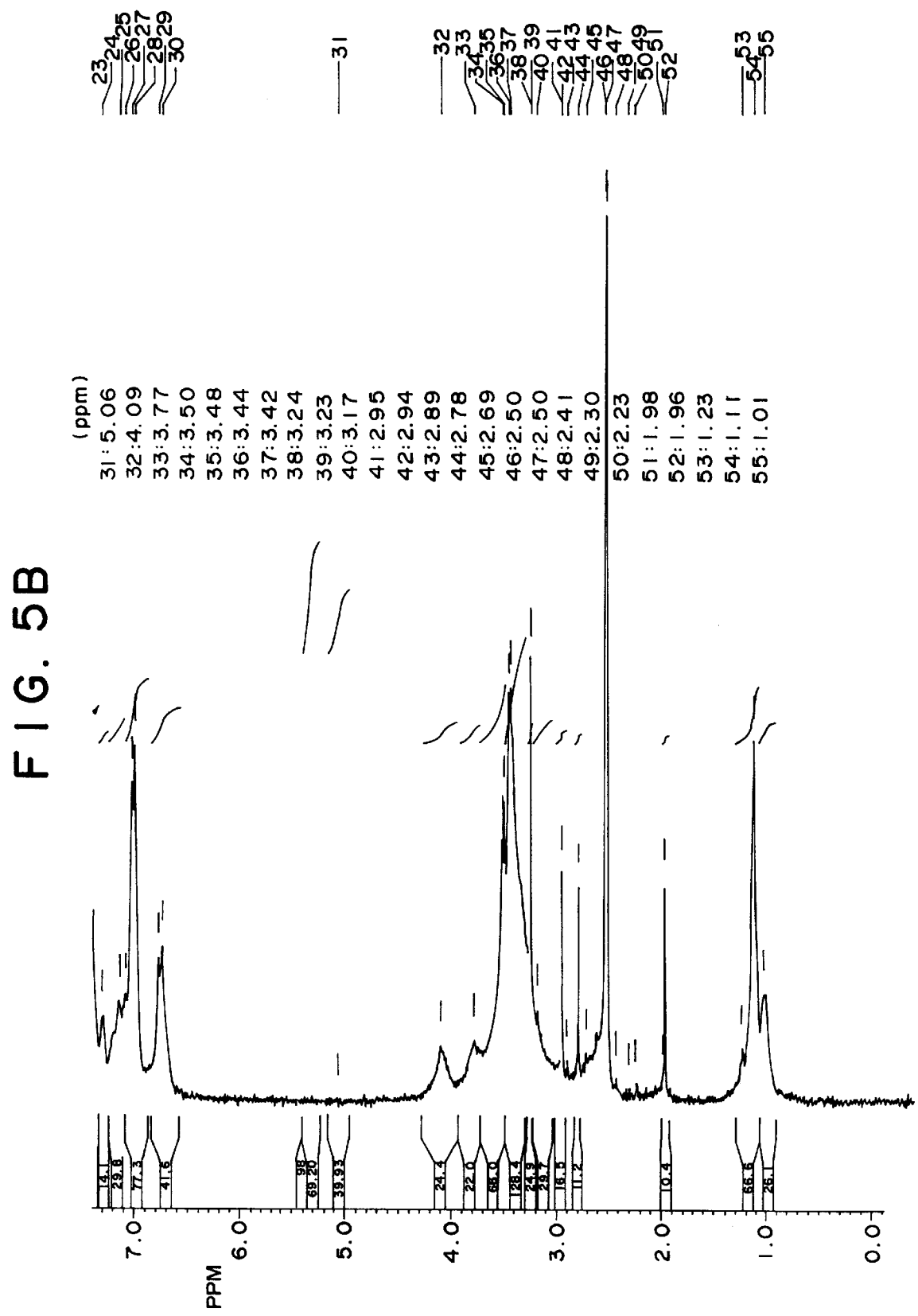

A small amount of this copolymer was dropwise added to water, and the solid deposited was collected by filtration, followed by drying under reduced pressure. $^1$H-NMR spectra measured using deuterated dimethyl sulfoxide (DMSO-$d_6$) are shown in FIGS. 5A and 5B.

Synthesis Example 8: Synthesis of polyimide precursor copolymer (dye density: 30.0%)

20.0 g of the polyimide precursor of Synthesis Example 5 and 11.9 g of a polyimide precursor solution obtained in the same manner as in Synthesis Example 6(1) were mixed. The procedure of Synthesis Example 7 was repeated to obtain 29.3 g of a copolymer polyimide precursor solution having a dye density of 30.0%.

Synthesis Example 9: Formation of polyimide film

The polyimide precursor solution obtained in Synthesis Example 5 was spin-coated on a silicon wafer of 5 inches diameter, having a surface formed of a silicon oxide layer, and the coating formed was heated to cure in an atmosphere of nitrogen, at 40° C. for 10 minutes, at 120° C. for 10 minutes and further at 270° C. for 10 minutes. As a result, a film, consisting of the polyimide, which has a repeating unit represented by the following chemical formula (14) was obtained.

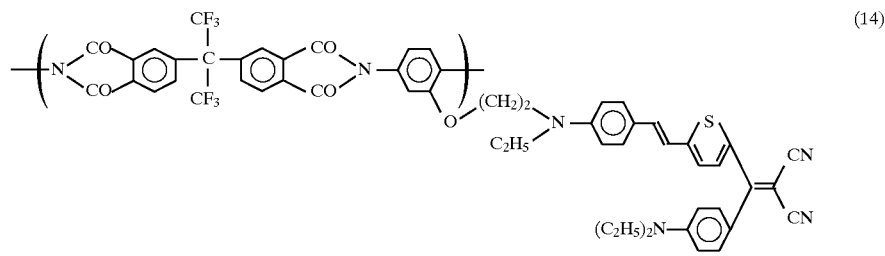

(14)

Example 1: Formation of polyimide copolymer film (dye density: 12.2%)

The polyimide precursor solution obtained in Synthesis Example 6 was spin-coated on a silicon wafer of 5 inches diameter, having a surface formed of a silicon oxide layer, and the coating formed was heated to cure in an atmosphere of nitrogen, at 40° C. for 10 minutes, at 120° C. for 10 minutes and further at 270° C. for 10 minutes to form a film, consisting of the polyimide, which has the repeating unit represented by the above chemical formula (14) and a repeating unit represented by the following chemical formula (15), and whose a dye density is 12.2%. The glass transition point, refractive index at 830 nm and light transmission loss of the polyimide film thus obtained were measured.

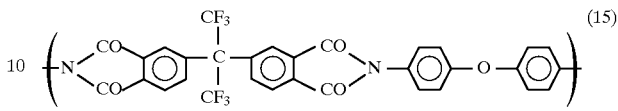

(15)

The polyimide precursor solution obtained in Synthesis Example 6 was also spin-coated on a glass substrate on the surface of which an ITO (indium tin oxide) film was formed by vacuum deposition, and the coating formed was heated to cure in an atmosphere of nitrogen, at 100° C. for 5 minutes and further at 200° C. for 5 minutes to obtain a polyimide film having a layer thickness of 4 µm. On the polyimide film thus obtained, an aluminum electrode (diameter: 3 mm) was formed by vacuum deposition, and was heated to cure at a poling temperature for 10 minutes while applying a poling voltage, where electro-optic constant $r_{33}$ at 830 nm was measured.

The results of measurement are shown in Table 1.

TABLE 1

| | | | Dye density | Tg | Transmission loss (dB/cm) | | Refractive index | | Poling conditions $r_{33}$ | | |
|---|---|---|---|---|---|---|---|---|---|---|---|
| | Dye | n | (wt. %) | (°C.) | TM | TE | TE | TC | Temp. (°C.) | Voltage (V/µm) | (pm/V) |
| Example: | | | | | | | | | | | |
| 1 | 4a | 2 | 12.2 | 267 | 3.0 | 3.2 | 1.6042 | 1.6120 | 285 | 90 | 2.5 |
| 2 | 4a | 2 | 20.0 | 250 | 4.2 | 3.8 | 1.6172 | 1.6247 | 262 | 90 | 4.0 |
| | | | | | | | | | 295 | 90 | 4.5 |
| 3 | 4a | 2 | 30.0 | 240 | 7.3 | 7.8 | 1.6500 | 1.6428 | 250 | 105 | 7.5 |
| 4 | 4b | 3 | 20.0 | 255 | | | | | 290 | 95 | 5.1 |
| 5 | 4d | 5 | 20.0 | 253 | | | | | 270 | 80 | 4.2 |
| 6 | 4e | 6 | 20.0 | 253 | | | | | 265 | 100 | 3.6 |
| | | | | | | | | | 280 | 100 | 5.2 |
| 7 | 2a | 2 | 13.0 | 260 | | | | | 280 | 90 | 4.0 |
| 8 | 2a | 2 | 10.0 | 110 | | | | | 120 | 90 | 3.1 |

Example 2: Formation of polyimide copolymer film (dye density: 20.0%)

A film of the polyimide copolymer having a dye density of 20.0% was formed in the same manner as in Example 1, but using the polyimide precursor solution obtained in Synthesis Example 7, and its characteristics were measured. The results of measurement are shown in Table 1.

Example 3: Formation of polyimide copolymer film (dye density: 20.0%)

A film of the polyimide copolymer having a dye density of 20.0% was formed in the same manner as in Example 1, but using the polyimide precursor solution obtained in Synthesis Example 8, and its characteristics were measured. The results of measurement are shown in Table 1.

Synthesis Example 10: Synthesis of Compound 1i (1) Synthesis of N-ethyl-N-[2-(methoxymethyl)oxyethyl]aniline:

55.7 g (0.34 mol) of N-ethyl-N-(2-hydroxylethyl)aniline was dissolved in 250 ml of anhydrous tetrahydrofuran, and 162 ml (1.2-fold equivalent weight) of a 2.5M hexane solution n-butyllithium was dropwise added thereto over a period of 30 minutes at 0° C. in an atmosphere of argon, followed by stirring at 0° C. for 30 minutes. Next, to the reaction solution obtained, 30.0 g (1.09-fold equivalent weight) of methoxymethyl chloride was dropwise added, and the solution was heated and refluxed for 12 hours, followed by cooling. The precipitate formed was removed by filtration, and thereafter the filtrate obtained was concentrated under reduced pressure. The oily residue thus obtained was distilled under reduced pressure to obtain 63 g of N-ethyl-N-[2-(methoxymethyl)oxyethyl]aniline (yield: 89%).

Boiling point: 98° C./0.1 Torr.; $^1$H-NMR Spectrum [δ (ppm)]: 1.16(t, 3H, J=6.9 Hz), 3.35(s, 3H), 3.41(q, 2H, J=6.9 Hz), 3.51(t, 2H, J=6.3 Hz), 3.69(t, 2H, J=6.3 Hz), 4.63(s, 2H), 6.51–6.71(m, 3H), 7.18–7.25(m, 2H)

(2) Synthesis of N-ethyl-N-[2-(methoxymethyl)oxyethyl]-4-bromoaniline:

46.5 g (0.22 mol) of N-ethyl-N-[2-(methoxymethyl)ethyl]aniline was dissolved in 280 ml of anhydrous DMF, and a solution prepared by dissolving 40.0 g (1.05-fold equivalent weight) of N-bromosuccinimide in 150 ml of anhydrous DMF was dropwise added thereto in an atmosphere of nitrogen, followed by stirring for 12 hours. The reaction solution obtained was poured into 1,000 ml of water, and was extracted with dichloromethane (2×200 ml). The organic layer was dried with anhydrous sodium sulfate, and thereafter concentrated under reduced pressure. The oily residue thus obtained was distilled under reduced pressure to obtain 57.5 g of N-ethyl-N-[2-(methoxymethyl)oxyethyl]-4-bromoaniline (yield: 89%).

Boiling point: 125° C./0.07 Torr.; $^1$H-NMR Spectrum [δ (ppm)]: 1.14(t, 3H, J=6.9 Hz), 3.34(s, 3H), 3.38(q, 2H, J=6.9 Hz), 3.48(t, 2H, J=6.3 Hz), 3.66(t, 2H, J=6.3 Hz), 4.61(s, 2H), 6.57(d, 2H, J=9.0 Hz), 7.26(d, 2H, J=9.0 Hz)

(3) Synthesis of N-ethyl-N-[2-(methoxymethyl)oxyethyl]-4-formylaniline:

68.0 g (0.23 mol) of N-ethyl-N-[2-(methoxymethyl)oxyethyl]-4-bromoaniline was dissolved in 500 ml of anhydrous THF in an atmosphere of nitrogen, and 280 ml (2.2-fold equivalent weight) of a 1.7M n-butyllithium solution (solvent: n-pentane) was dropwise added thereto at −78° C., followed by stirring for 45 minutes. To the reaction solution obtained, 25 ml of anhydrous DMF was added, and the solution was stirred for 8 hours while allowing the temperature to naturally rise to room temperature. Thereafter, 100 ml of water was added to the resulting reaction solution, which was then extracted with dichloromethane (100 ml×2). The organic layer was dried with anhydrous sodium sulfate, and thereafter concentrated under reduced pressure. The residue thus obtained was distilled under reduced pressure to obtain 51.0 g of N-ethyl-N-[2-(methoxymethyl)oxyethyl]-4-formylaniline (yield: 91%).

$^1$H-NMR Spectrum [δ (ppm)]: 1.22(t, 3H, J=7.2 Hz), 3.34(s, 3H), 3.52(q, 2H, J=7.2 Hz), 3.61(t, 2H, J=6.1 Hz), 3.73(t, 2H, J=6.1 Hz), 4.63(s, 2H), 6.73(d, 2H, J=8.7 Hz), 7.72(d, 2H, J=8.7 Hz), 9.72(s, 1H)

(4) Synthesis 2-{N-ethyl-N-[2-(methoxymethyl)oxyethyl]anilin-4-yl}vinylthiophene:

10.0 g (42.1 mmols) of N-ethyl-N-[2-(methoxymethyl)oxyethyl]-4-formylaniline and 10.76 g (1.01-fold equivalent weight) of 2-thienylmethyl diethoxyphosphate were dissolved in 200 ml of anhydrous THF, and 5.2 g (1.1-fold equivalent weight) of potassium t-butoxide was added thereto in an atmosphere of argon, followed by stirring at room temperature for 12 hours while shielding light. The resulting reaction solution was concentrated under reduced pressure. The residue thus obtained was dissolved in 300 ml of dichloromethane, followed by washing with water (200 ml×3). The organic layer obtained was dried with anhydrous sodium sulfate, and then concentrated under reduced pressure. The residue obtained was purified by silica gel column chromatography (developing system: hexane/ethyl acetate=4/1 to 1/1) to obtain 12.1 g of 2-{N-ethyl-N-[2-(methoxymethyl)oxyethyl]anilin-4-yl}vinylthiophene (yield: 90%); $^1$H-NMR Spectrum [δ (ppm)]: 1.11(t, 3H, J=7.2 Hz), 3.28(s, 3H), 3.37(q, 2H, J=7.2 Hz), 3.47(t, 2H, J=6.1 Hz), 3.63(t, 2H, J=6.1 Hz), 4.56(s, 2H), 6.68(d, 2H, J=9.0 Hz), 6.86(d, 1H, J=16.2 Hz), 6.96–6.99(m, 2H), 7.03(d, 1H, J=16.2 Hz), 7.10–7.12(m, 1H), 7.34(d, 2H, J=9.0 Hz)

(5) Synthesis of compound 1i:

5.0 g (15.75 mmols) of 2-{N-ethyl-N-[2-(methoxymethyl)oxyethyl]anilin-4-yl}vinylthiophene was dissolved in 150 ml of anhydrous THF in an atmosphere of nitrogen, and 6.4 ml (1.01-fold equivalent weight) of t-butyllithium (2.5M, a hexane solution) was dropwise added thereto, followed by stirring for 2 hours. The solution obtained was further stirred at −50° C. for 2 hours and also stirred at −20° to −15° C. for 2 hours. Thereafter, 3.94 g (1.0-fold equivalent weight) of N,N-diethyl-4-tricyanovinylaniline was added at −78° C., followed by stirring for 12 hours while allowing the temperature to naturally rise to room temperature. The resulting reaction solution was concentrated, and the residue thus obtained was purified by silica gel column chromatography (developing system: hexane/ethyl acetate/dichloromethane=2/0/1→1/0/5→4/1/1→4/2/2) to obtain 7.8 g of the compound 1i (yield: 92%).

$^1$H-NMR Spectrum [δ (ppm)]: 1.17(t, 3H, J=6.9 Hz), 1.23(t, 6H, J=6.9 Hz), 3.28(s, 3H), 3.37(q, 6H, J=6.9 Hz), 3.49(t, 2H, J=5.7 Hz), 3.64(t, 2H, J=5.7 Hz), 4.56(s, 2H), 6.60(d, 2H, J=9.0 Hz), 6.65(d, 2H, J=9.0 Hz), 6.88(d, 1H, 16.2 Hz), 6.95(d, 1H, J=16.2 Hz), 6.99(d, 1H, J=4.2 Hz), 7.27(d, 2H, J=9.0 Hz), 7.37(d, 2H, J=9.0 Hz), 7.57(d, 1H, J=4.2 Hz)

Synthesis Example 11: Synthesis of compound 2a 5.40 g (10.0 mmols) of the compound 1i was dissolved in 100 ml of THF, and 100 ml of 6N hydrochloric acid was added thereto. The solution obtained was heated for 3 hours at 60° C. in an atmosphere of nitrogen, and thereafter cooled with ice. To the reaction solution obtained, a solution of 42 g of potassium carbonate in 200 ml of water was dropwise added while cooling with ice, followed by stirring for 1 hour. Thereafter, the resulting solution was separated to take out an organic layer, which was then dried with anhydrous sodium sulfate, and thereafter concentrated under reduced pressure. The residue thus obtained was purified by silica gel column chromatography (developing system: dichloromethane/ethyl acetate=100/1→10/1) to obtain 3.87 g of the same compound 2a as that of Synthesis Example 2 (yield: 78%).

II. Synthesis of Polyimide Precursor or Polyimide (n=3)

Synthesis Example 12: Synthesis of Compound 1b (1) Synthesis of N-ethyl-N-(3-hydroxypropyl)-4-bromoaniline:

Synthesized in the same manner as the step (3) in Synthesis Example 1, but from 15.0 g (75.0 mmols) of N-ethyl-N-bromoaniline and 7.96 ml (1.2-fold equivalent weight) of 3-bromopropanol (amount: 15.0 g; yield: 73%).

IR Spectrum [ν (cm$^{-1}$)]: 3336, 2932, 2880, 1588, 1542, 1492, 1458, 1350, 1266, 1176, 1122, 1050, 792; $^1$H-NMR Spectrum [δ (ppm)]: 1.12(t, 3H, J=7.1 Hz), 1.67(brs, 1H), 1.84(quint, 2H, J=7.53 Hz), 3.34(m, 4H), 3.72(t, 2H, J=5.9 Hz), 6.59(d, 2H, J=9.1 Hz), 7.26(d, 2H, J=9.1 Hz)

(2) Synthesis of N-ethyl-N-[3-(tetrahydropyran-2-yl)oxypropyl]4-bromoaniline:

Synthesized in the same manner as the step (4) in Synthesis Example 1, but from 15.0 g (54.7 mmols) of N-ethyl-N-[3-hydroxypropyl)-4-bromoaniline (amount: 18.7 g; yield: quantitative).

IR Spectrum [ν (cm$^{-1}$)]: 2932, 2872, 1588, 1492, 1348, 1262, 1180, 1118, 1062, 1030, 986, 902, 864, 798; $^1$H-NMR Spectrum [δ (ppm)]: 1.15(t, 3H, J=6.9 Hz), 1.51–1.68(m, 4H), 1.68–2.00(m, 4H), 3.26–3.55(m, 6H), 3.75–3.90(m, 2H), 4.57(t, 1H, J=3.2 Hz), 6.56(d, 2H, J=9.0 Hz), 7.24(d, 2H, J=9.0 Hz)

(3) Synthesis of N-ethyl-N-[3-(tetrahydropyran-2-yl)oxypropyl]4-formylaniline:

Synthesized in the same manner as the step (5) in Synthesis Example 1, but from 17.2 g (50.2 mmols) of N-ethyl-N-[3-(tetrahydropyran-2-yl)oxypropyl)-4-bromoaniline (amount: 14.2 g; yield: 92%).

IR Spectrum [ν (cm$^{-1}$)]: 2928, 2724, 1666, 1592, 1552, 1524, 1434, 1404, 1350, 1312, 1276, 1234, 1160, 1064, 1020, 800; $^1$H-NMR Spectrum [δ (ppm)]: 1.21(t, 3H, J=7.1 Hz), 1.46–1.68(m, 4H), 1.17–2.00(m, 4H), 3.39–3.55(m, 6H), 3.73–3.91(m, 2H), 4.58(t, 1H, J=3.3 Hz), 6.72(d, 2H, J=9.1 Hz), 7.70(d, 2H, J=9.1 Hz), 9.70(s, 1H)

(4) Synthesis of 2-{N-ethyl-N-[3-(tetrahydropyran-2-yl)oxypropyl]anilin-4-yl}vinylthiophene:

Synthesized in the same manner as the step (6) in Synthesis Example 1, but using 14.0 g (48.0 mmols) of N-ethyl-N-[3-(tetrahydropyran-2-yl)oxypropyl)-4-formylaniline as the formyl component (amount: 17.8 g; yield: quantitative).

IR Spectrum [ν (cm$^{-1}$)]: 2928, 1600, 1512, 1436, 1350, 1262, 1174, 1118, 1062, 1030, 946, 844, 810, 680; $^1$H-NMR Spectrum [δ (ppm)]: 1.16(t, 3H, J=7.0 Hz), 1.57(m, 4H), 1.70–1.80(m, 1H), 1.89(m, 3H), 3.41(m, 6H), 3.85(m, 2H), 4.58(t, 1H, J=3.5 Hz), 6.66(d, 2H, J=8.9 Hz), 6.85(d, 1H, J=16.0 Hz), 6.96(m, 2H), 7.01(d, 1H, J=16.0 Hz), 7.09(m, 1H), 7.32(d, 2H, J=8.9 Hz)

(5) Synthesis of compound 1b:

Compound 1b was obtained in an amount of 13.5 g (yield: 47%) in the same manner as the step (8) in Synthesis Example 1, but using 17.5 g (47.1 mmols) of 2-{N-ethyl-N-[3-(tetrahydropyran-2-yl)oxypropyl]anilin-4-yl}vinylthiophene as the thiophene component.

IR Spectrum [ν (cm$^{-1}$)]: 2928, 2196, 1590, 1510, 1470, 1400, 1336, 1270, 1174, 1030, 796; $^1$H-NMR Spectrum [δ (ppm)]: 1.20(m, 9H), 1.58(m, 5H), 1.68–1.80(m, 1H), 1.89 (m, 2H), 3.45(m, 10H), 3.83(m, 2H), 4.58(s, 1H), 6.67(d, 4H, J=8.9 Hz), 6.94(d, 1H, J=16.0 Hz), 7.02(d, 1H, J=16.0 Hz), 7.05(d, 1H, J=4.1 Hz), 7.33(d, 2H, J=8.9 Hz), 7.43(d, 2H, J=8.9 Hz), 7.63(d, 1H, J=4.1 Hz)

Synthesis Example 13: Synthesis of compound 2b

Compound 2b was obtained in an amount of 11.5 g (yield: quantitative) in the same manner as in Synthesis Example 2, but using 13.5 g (22.6 mmols) of the compound 1b as the tetrahydropyranyl component.

IR Spectrum [ν (cm$^{-1}$)]: 3444, 2874, 2324, 2196, 1588, 1506, 1468, 1400, 1338, 1270, 1170, 1150, 1048, 942, 794; $^1$H-NMR Spectrum [δ (ppm)]: 1.21(m, 9H), 1.86(quint, 2H, J=6.5 Hz), 3.43(m, 8H), 3.74(t, 2H, J=5.9 Hz), 6.67(dd, 4H, J=2.9 Hz, 9.0 Hz), 6.94(d, 1H, J=15.9 Hz), 7.02(d, 1H, J=15.9 Hz), 7.05(d, 1H, J=4.1 Hz), 7.34(d, 2H, J=8.8 Hz), 7.43(d, 2H, J=9.0 Hz), 7.63(d, 1H, J=4.1 Hz)

Synthesis Example 14: Synthesis of compound 3b

Compound 3b was obtained in an amount of 6.9 g (yield: 84.5%) in the same manner as in Synthesis Example 3, but using 6.2 g (12.1 mmols) of the compound 2b.

IR Spectrum [ν (cm$^{-1}$)]: 2936, 2200, 1594, 1522, 1402, 1338, 1264, 1176, 1062, 808, 730; $^1$H-NMR Spectrum [δ (ppm)]: 1.22(m, 9H), 2.18(quint, 2H, J=5.7 Hz), 3.45(m, 6H), 3.60(t, 2H, J=7.0 Hz), 4.27(t, 2H, J=5.5 Hz), 6.67(d, 2H, J=9.1 Hz), 6.70(d, 2H, J=8.9 Hz), 6.94(d, 1H, J=16.0 Hz), 7.02(d, 1H, J=16.0 Hz), 7.06(d, 1H, J=4.1 Hz), 7.33(d, 2H, J=8.9 Hz), 7.44(d, 2H, J=9.1 Hz), 7.63(d, 1H, 4.1 Hz), 7.94(m, 3H)

Synthesis Example 15: Synthesis of compound 4b

Compound 4b was obtained in an amount of 4.1 g (yield: 67%) in the same manner as in Synthesis Example 4, but using 6.8 g (10.0 mmols) of the compound 3b.

IR Spectrum [ν (cm$^{-1}$)]: 3412, 2932, 2200, 1590, 1508, 1468, 1400, 1336, 1272, 1174, 1050, 946, 798; $^1$H-NMR Spectrum [δ (ppm)]: 1.23(m, 9H), 2.10(quint, 2H, J=6.2 Hz), 2.80–3.70(brs, 4H), 3.43(m, 6H), 3.55(t, 2H, J=7.0 Hz), 4.00(t, 2H, J=5.7 Hz), 6.20(dd, 1H, J=2.3 Hz, 8.1 Hz), 6.24(d, 1H, J=2.3 Hz), 6.60(d, 1H, J=7.9 Hz), 6.67(t, 4H, J=9.0 Hz), 6.94(d, 1H, J=16.0 Hz), 7.02(d, 1H, J=16.0 Hz), 7.05(d, 1H, J=4.2 Hz), 7.33(d, 2H, J=9.0 Hz), 7.43(d, 2H, J=9.0 Hz), 7.63(d, 1H, 4.2 Hz)

Synthesis Example 16: Synthesis of polyimide precursor

A polyimide precursor solution (solid content: 15% by weight) was obtained in an amount of 10.9 g in the same manner as in Synthesis Example 5, but using 1.0 g (1.62 mmols) of the compound 4b as the diamine.

Synthesis Example 17: Synthesis of polyimide precursor copolymer

A polyimide precursor copolymer solution having a dye density of 20.0% was obtained in an amount of 34.1 g (solid content: 15% by weight) in the same manner as in Synthesis Example 6(2), but using 15.0 g of the polyimide precursor solution obtained in Synthesis Example 16 and 22.1 g of a polyimide precursor solution obtained in the same manner as in Synthesis Example 6(1).

Synthesis Example 18: Formation of polyimide film

Heat curing was carried out in the same manner as in Synthesis Example 9, but using the polyimide precursor solution obtained in Synthesis Example 16. As a result, a film consisting of the polyimide having a repeating unit represented by the following chemical formula (16) was obtained.

fold equivalent weight) of N-diisopropylethylamine were mixed, and the mixture obtained was heated at 130° C. for 12 hours in an atmosphere of argon. Next, 100 ml of water was added to the reaction solution obtained, which was then

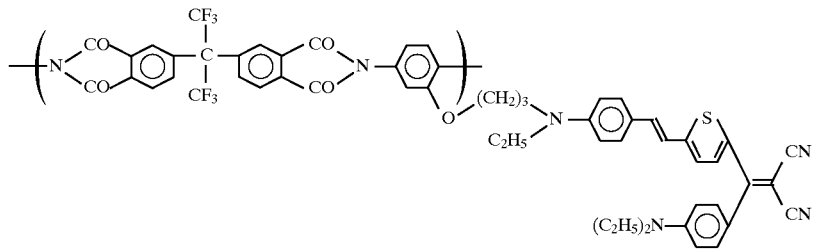

(16)

Example 4: Formation of polyimide copolymer film

A film of polyimide having the repeating unit represented by the above chemical formula (16) and a repeating unit represented by the chemical formula (15) and having a dye density of 20.0% was formed in the same manner as in Example 1, but using the polyimide precursor solution obtained in Synthesis Example 17, and its characteristics were measured. The results of measurement are shown in Table 1.

III. Synthesis of Polyimide Precursor or Polyimide (n=4)

Synthesis Example 19: Synthesis of compound 1c (1) Synthesis of 4-bromobutanol:

20.0 g (222.0 mmols) of 1,4-butanediol and 58.2 g (1.0-fold equivalent weight) of triphenylphosphine were weighed out, and were dissolved in 110 ml of tetrahydrofuran. To the solution obtained, 73.6 g (1.0-fold equivalent weight) of carbon tetrabromide was gradually added at 0° C., followed by stirring for 1 hour. The resulting reaction solution was concentrated, and the residue thus obtained was purified by silica gel column chromatography (developing system: hexane/ethyl acetate=2/1) to obtain 16.2 g of 4-bromobutanol (yield: 47.8%).

IR Spectrum [ν (cm$^{-1}$)]: 3276, 2940, 1704, 1430, 1362, 1242, 1032; $^1$H-NMR Spectrum [δ (ppm)]: 1.70(m, 2H), 1.95(m, 2H), 3.46(t, 2H, J=6.7 Hz), 3.64(t, 2H, J=6.4 Hz), 4.08(s, 1H)

(2) Synthesis of 4-(tetrahydropyran-2-yl)oxybutyl bromide:

16.0 g (105.0 mmols) of 4-bromobutanol was dissolved in 140 ml of chloroform, and a solution prepared by dissolving 13.9 ml (1.5-fold equivalent weight) of 3,4-dihydro-2H-pyran in 40 ml of chloroform was dropwise added thereto at 0° C. in an atmosphere of argon. The solution obtained was stirred for 4 hours while keeping it at 0° C., followed by addition of an aqueous sodium hydrogencarbonate, and the resulting solution was extracted with chloroform (100 ml×2). The organic layer obtained was dried with anhydrous sodium sulfate, and thereafter concentrated under reduced pressure to obtain 24.0 g of 4-(tetrahydropyran-2-yl)oxybutyl bromide (yield: 96%).

IR Spectrum [ν (cm$^{-1}$)]: 2928, 2870, 1736, 1436, 1346, 1234, 1198, 1116, 1060, 1022, 862, 808; $^1$H-NMR Spectrum [δ (ppm)]: 1.49–1.59(m, 4H), 1.69–1.92(m, 4H), 1.92–2.05(m, 2H), 3.40–3.54(m, 4H), 3.72–3.88(m, 2H), 4.57(t, 1H, J=6.2 Hz)

(3) Synthesis of N-ethyl-N-[4-(tetrahydropyran-2-yl) oxybutyl]-4-bromoaniline 9.6 g (47.8 mmols) of N-ethyl-4-bromoaniline, 17.0 g (1.5-fold equivalent weight) of 4-(tetrahydropyran-2-yl)oxybutyl bromide and 37.5 ml (4.5- extracted with ethyl acetate (100 ml×3). The organic layer obtained was dried with anhydrous sodium sulfate, and thereafter concentrated under reduced pressure. The residue thus obtained was purified by silica gel column chromatography (developing system: chloroform/hexane=2/1) to obtain 10.5 g of N-ethyl-N-[4-(tetrahydropyran-2-yl) oxybutyl]-4-bromoaniline (yield: 62%).

IR Spectrum [ν (cm$^{-1}$)]: 2928, 2868, 1588, 1490, 1352, 1262, 1180, 1116, 1064, 1020, 900, 866, 796; $^1$H-NMR Spectrum [δ (ppm)]: 1.15(t, 3H, J=6.9 Hz), 1.51–1.90(m, 10H), 3.23–3.54(m, 6H), 3.73–3.90(m, 2H), 4.57(t, 1H, Hz), 6.53(d, 2H, J=9.0 Hz), 7.24(d, 2H, 9.0 Hz)

(4) Synthesis of N-ethyl-N-[4-(tetrahydropyran-2-yl) oxybutyl]-4-formylaniline:

Synthesized in the same manner as the step (5) in Synthesis Example 1, but using 10.0 g (28.0 mmols) of N-ethyl-N-[4-(tetrahydropyran-2-yl)oxybutyl)-4-bromoaniline as the bromo component. (amount: 6.0 g; yield: 71%).

IR Spectrum [ν (cm$^{-1}$)]: 2932, 2876, 2728, 1664, 1590, 1552, 1524, 1436, 1402, 1350, 1312, 1272, 1236, 1198, 1158, 1068, 1020, 894, 864, 808; $^1$H-NMR Spectrum [δ (ppm)]: 1.20(t, 3H, J=7.1 Hz), 1.48–1.88(m, 10H), 3.36–3.55(m, 6H), 3.78–3.91(m, 2H), 4.58(t, 1H, J=3.3 Hz), 6.69(d, 2H, J=9.0 Hz), 7.70(d, 2H, J=9.0 Hz), 9.70(s, 1H)

(5) Synthesis of 2-{N-ethyl-N-[4-(tetrahydropyran-2-yl) oxybutyl]anilin-4-yl}vinylthiophene:

Synthesized in the same manner as the step (6) in Synthesis Example 1, but using 6.0 g (19.6 mmols) of N-ethyl-N-[4-(tetrahydropyran-2-yl)oxybutyl)-4-formylaniline as the formyl component (amount: 6.6 g; yield: 87%).

IR Spectrum [ν (cm$^{-1}$)]: 2928, 1602, 1512, 1400, 1358, 1262, 1176, 1118, 1066, 1020, 944, 850, 800, 682; $^1$H-NMR Spectrum [δ (ppm)]: 1.15(t, 3H, J=7.0 Hz), 1.38–1.88(m, 10H), 3.28–3.54(m, 6H), 3.74–3.91(m, 2H), 4.58(t, 1H, J=3.4 Hz), 6.62(d, 2H, J=8.8 Hz), 6.84(d, 1H, J=16.0 Hz), 6.97(s, 2H), 7.01(d, 1H, J=16.0 Hz), 7.09(m, 1H), 7.32(d, 2H, J=8.8 Hz)

(6) Synthesis of compound 1c:

Compound 1c was obtained in an amount of 9.6 g (yield: 87%) in the same manner as the step (8) in Synthesis Example 1, but using 6.6 g (17.0 mmols) of 2-{N-ethyl-N-[4-(tetrahydropyran-2-yl)oxybutyl]anilin-4-yl}vinylthiophene as the thiophene component.

IR Spectrum [ν (cm$^{-1}$)]: 2912, 2860, 2340, 2196, 1588, 1506, 1472, 1402, 1342, 1260, 1174, 1148, 1054, 946, 792, 516; $^1$H-NMR Spectrum [δ (ppm)]: 1.22(m, 9H), 1.40–1.90 (m, 10H), 3.25–3.60(m, 10H), 3.82(m, 2H), 4.58(t, 1H, J=3.3 Hz), 6.65(t, 4H, J=8.1 Hz), 6.94(d, 1H, J=16.0 Hz), 7.02(d, 1H, J=16.0 Hz), 7.04(d, 1H, J=4.1 Hz), 7.33(d, 2H, J=8.1 Hz), 7.43(d, 2H, J=8.1 Hz), 7.62(d, 1H, J=4.1 Hz)

Synthesis Example 20: Synthesis of compound 2c

Compound 2c was obtained in an amount of 6.7 g (yield: 86%) in the same manner as in Synthesis Example 2, but using 9.6 g (14.8 mmols) of the compound 1c as the tetrahydropyranyl component.

IR Spectrum [ν (cm$^{-1}$)]: 3488, 2920, 2332, 2200, 1592, 1508, 1470, 1402, 1338, 1298, 1270, 1168, 1050, 946, 794;

$^1$H-NMR Spectrum [δ (ppm)]: 1.20(m, 9H), 1.64(m, 4H), 3.43(m, 8H), 3.70(t, 2H, J=6.0 Hz), 6.65(t, 4H, J=8.8 Hz), 6.94(d, 1H, J=15.9 Hz), 7.02(d, 1H, J=15.9 Hz), 7.05(d, 1H, J=4.1 Hz), 7.33(d, 2H, J=8.8 Hz), 7.43(d, 2H, J=8.9 Hz), 7.63(d, 1H, J=4.1 Hz)

Synthesis Example 21: Synthesis of compound 3c

Compound 3c was obtained in an amount of 730 mg (yield: 47%) in the same manner as in Synthesis Example 3, but using 1.2 g (2.3 mmols) of the compound 2c.

IR Spectrum [ν (cm$^{-1}$)]: 2934, 2200, 1594, 1522, 1402, 1338, 1264, 1178, 1060, 796, 730; $^1$H-NMR [δ (ppm)]: 1.23(m, 9H), 1.91(m, 4H), 3.42(m, 8H), 4.24(t, 2H, J=5.65 Hz), 6.65(m, 4H), 6.94(d, 1H, J=16.0 Hz), 7.02(d, 1H, J=16.0 Hz), 7.05(d, 1H, J=4.1 Hz), 7.33(d, 2H, J=8.8 Hz), 7.43(d, 2H, J=9.0 Hz), 7.63(d, 1H, J=4.1 Hz), 7.90(m, 2H)

Synthesis Example 22: Synthesis of compound 4c

Compound 4c was obtained in an amount of 1.2 g (yield: 67%) in the same manner as in Synthesis Example 4, but using 2.0 g (2.9 mmols) of the compound 3c as the dinitro component.

IR Spectrum [ν (cm$^{-1}$)]: 2884, 2328, 2200, 1588, 1506, 1470, 1398, 1336, 1296, 1268, 1172, 1050, 952, 798; $^1$H-NMR Spectrum [δ (ppm)]: 1.22(m, 9H), 1.83(brs, 4H), 2.80–3.70(brs, 4H), 3.42(m, 8H), 3.98(t, 2H, J=5.63 Hz), 6.19(dd, 1H, J=2.3 Hz, 8.3 Hz), 6.25(d, 1H, J=2.3 Hz), 6.58(d, 1H, J=8.3 Hz), 6.65(t, 4H, J=8.9 Hz), 6.94(d, 1H, J=16.0 Hz), 7.02(d, 1H, J=16.0 Hz), 7.05(d, 1H, J=4.2 Hz), 7.33(d, 2H, J=8.9 Hz), 7.43(d, 2H, J=8.9 Hz), 7.63(d, 1H, J=4.2 Hz)

Synthesis Example 23: Synthesis of polyimide precursor

A polyimide precursor solution was obtained in an amount of 10.8 g (solid content: 15% by weight) in the same manner as in Synthesis Example 5, but using 1.0 g (1.59 mmols) of the compound 4c as the diamine.

Synthesis Example 24: Synthesis of polyimide precursor copolymer

A mixed polyimide precursor copolymer solution having a dye density of 20.0% was obtained in an amount of 27.6 g (solid content: 15% by weight) in the same manner as in Synthesis Example 6(2), but using 11.8 g of the polyimide precursor solution obtained in Synthesis Example 23 and 18.2 g of a polyimide precursor solution obtained in the same manner as in Synthesis Example 6(1). The stirring at 65° C. was carried out for 2 hours and 15 minutes.

Synthesis Example 25: Formation of polyimide film

Heat curing was carried out in the same manner as in Synthesis Example 9, but using the polyimide precursor solution obtained in Synthesis Example 23. As a result, a film consisting of the polyimide having a repeating unit represented by the following chemical formula (17) was obtained.

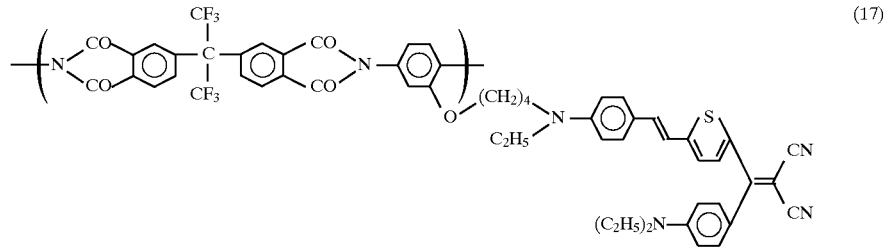

(17)

Synthesis Example 26: Formation of polyimide copolymer film

Heat curing was carried out in the same manner as in Synthesis Example 9, but using the polyimide precursor solution obtained in Synthesis Example 25. As a result, a film consisting of the polyimide having the repeating unit represented by the above chemical formula (17) and the repeating unit represented by the chemical formula (15) and having a dye density of 20.0% was formed.

IV. Synthesis of Polyimide Precursor or Polyimide (n=5)

Synthesis Example 27: Synthesis of compound 1d (1) Synthesis of 5-(tetrahydropyran-2-yl)oxypentyl bromide:

The procedure of the step (2) in Synthesis Example 19 was repeated except that as the starting material the 4-bromobutanol was replaced with 11.24 g of 5-bromopentanol. Thus, 18.0 g of crude 5-(tetrahydropyran-2-yl)oxypentyl bromide was obtained (theoretical amount: 16.9 g; content: 93.8%).

IR Spectrum [ν (cm$^{-1}$)]: 2924, 2868, 1736, 1438, 1344, 1248, 1116, 1062, 1020, 900, 868, 810; $^1$H-NMR Spectrum [δ (ppm)]: 1.35–1.72(m, 9H), 1.72–1.95(m, 4H), 3.44(t, 2H, J=6.8 Hz), 3.52(m, 1H), 3.71–3.90(m, 2H), 4.57(t, 1H, J=6.1 Hz)

(2) Synthesis of N-ethyl-N-[5-(tetrahydropyran-2-yl)oxypentyl]-4-bromoaniline

Synthesized in the same manner as the step (3) in Synthesis Example 19, except that the 4-(tetrahydropyran-2-yl)oxybutyl bromide was replaced with 17.5 g (content: 16.4 g; 1.5-fold equivalent weight) of the crude 5-(tetrahydropyran-2-yl)oxypentyl bromide obtained in the step (1) (amount: 10.9 g; yield: 66%).

IR Spectrum [ν (cm$^{-1}$)]: 2924, 2872, 1588, 1490, 1352, 1256, 1176, 1118, 1070, 1020, 900, 864, 796; $^1$H-NMR Spectrum [δ (ppm)]: 1.12(t, 3H, J=6.9 Hz), 1.35–1.90(m, 13H), 3.19–3.51(m, 5H), 3.70–3.88(m, 2H), 4.56(s, 1H), 6.51(d, 2H, J=7.6 Hz), 7.24(d, 2H, J=7.6 Hz)

(3) Synthesis of N-ethyl-N-[5-(tetrahydropyran-2-yl)oxypentyl]4-formylaniline:

Synthesized in the same manner as the step (5) in Synthesis Example 1, but using 10.5 g (28.3 mmols) of N-ethyl-N-[5-(tetrahydropyran-2-yl)oxypentyl)-4-bromoaniline as the bromo component. (amount: 8.0 g; yield: 89%).

IR Spectrum [ν (cm$^{-1}$)]: 2928, 2872, 2728, 1664, 1592, 1552, 1522, 1436, 1404, 1352, 1312, 1274, 1236, 1200, 1156, 1072, 1020, 810; $^1$H-NMR Spectrum [δ (ppm)]:

1.20(t, 3H, J=6.8 Hz), 1.35–1.90(m, 13H), 3.19–3.65(m, 5H), 3.70–3.90(m, 2H), 4.57(t, 1H, J=3.3 Hz), 6.65(d, 2H, J=9.0 Hz), 7.70(d, 2H, J=9.0 Hz), 9.89(s, 1H)

(4) Synthesis of 2-{N-ethyl-N-[5-(tetrahydropyran-2-yl)oxypentyl]anilin-4-yl}vinylthiophene:

Synthesized in the same manner as the step (6) in Synthesis Example 1, but using 8.0 g (25.0 mmols) of N-ethyl-N-[5-(tetrahydropyran-2-yl)oxypentyl]-4-formylaniline as the formyl component (amount: 8.8 g; yield: 88%).

IR Spectrum [ν (cm$^{-1}$)]: 2928, 1598, 1508, 1432, 1350, 1258, 1172, 1120, 1064, 1022, 946, 902, 844, 796, 680; $^1$H-NMR Spectrum [δ (ppm)]: 1.15(t, 3H, J=7.0 Hz), 1.38–1.88(m, 13H), 3.24–3.54(m, 5H), 3.71–3.89(m, 2H), 4.57(t, 1H, J=3.4 Hz), 6.62(d, 2H, J=8.8 Hz), 6.84(d, 1H, J=16.0 Hz), 6.99(s, 2H), 7.01(d, 1H, J=16.0 Hz), 7.09(m, 1H), 7.32(d, 2H, J=8.8 Hz)

(5) Synthesis of compound 1d:

Compound 1d was obtained in an amount of 10.0 g (yield: 81%) in the same manner as the step (8) in Synthesis Example 1, but using 8.8 g (22.0 mmols) of 2-{N-ethyl-N-[5-(tetrahydropyran-2-yl)oxypentyl]anilin-4-yl}vinylthiophene as the tetrahydropyranyl component.

IR Spectrum [ν (cm$^{-1}$)]: 2924, 2200, 1590, 1512, 1472, 1402, 1338, 1270, 1170, 1050, 1028, 796; $^1$H-NMR Spectrum [δ (ppm)]: 1.23(m, 9H), 1.39–1.84(m, 12H), 3.27–3.52 (m, 10H), 3.71–3.90(m, 2H), 4.57(t, 1H, J=3.4 Hz), 6.62(d, 2H, J=8.9 Hz), 6.67(t, 2H, J=9.1 Hz), 6.94(d, 1H, J=16.4 Hz), 7.02(d, 1H, J=16.4 Hz), 7.05(d, 1H, J=4.2 Hz), 7.33(d, 2H, J=8.9 Hz), 7.43(d, 2H, J=9.1 Hz), 7.63(d, 1H, J=4.2 Hz)

Synthesis Example 28: Synthesis of compound 2d

Compound 2d was obtained in an amount of 7.4 g (yield: 78.7%) in the same manner as in Synthesis Example 2, but from 10.8 g (17.3 mmols) of the compound 1d.

IR Spectrum [ν (cm$^{-1}$)]: 3440, 2908, 2340, 2200, 1588, 1506, 1470, 1400, 1336, 1294, 1270, 1152, 1048, 948, 794; $^1$H-NMR Spectrum [δ (ppm)]: 1.22(m, 9H), 1.45(m, 2H), 1.62(m, 4H), 3.31(t, 2H, J=7.5 Hz), 3.42(m, 6H), 3.67(t, 2H, J=6.4 Hz), 6.61(d, 2H, J=8.9 Hz), 6.66(d, 2H, J=9.1 Hz), 6.93(d, 1H, J=15.9 Hz), 7.01(d, 1H, J=15.9 Hz), 7.05(d, 1H, J=4.1 Hz), 7.33(d, 2H, J=8.9 Hz), 7.43(d, 2H, J=9.1 Hz), 7.63(d, 1H, J=4.1 Hz)

Synthesis Example 29: Synthesis of compound 3d

Compound 3d was obtained in an amount of 8.6 g (yield: 92%) in the same manner as in Synthesis Example 3, but using 7.2 g (13.4 mmols) of the compound 2d as the alcohol component.

IR Spectrum [ν (cm$^{-1}$)]: 2932, 2200, 1592, 1524, 1470, 1402, 1342, 1264, 1172, 1056, 1000, 952, 806, 726; $^1$H-NMR Spectrum [δ (ppm)]: 1.24(m, 9H), 1.57(m, 2H), 1.69(m, 2H), 1.94(quint, 2H, J=7.1 Hz), 3.42(m, 8H), 4.23(t, 2H, J=6.1 Hz), 6.63(d, 2H, J=8.8 Hz), 6.68(d, 2H, J=9.0 Hz), 6.94(d, 1H, J=16.0 Hz), 7.02(d, 1H, J=16.0 Hz), 7.06(d, 1H, J=4.1 Hz), 7.33(d, 2H, J=8.8 Hz), 7.45(d, 2H, J=9.0 Hz), 7.64(d, 1H, J=4.1 Hz), 7.91(brs, 2H)

Synthesis Example 30: Synthesis of compound 4d

Compound 4d was obtained in an amount of 5.6 g (yield: 72%) in the same manner as in Synthesis Example 4, but using 8.5 g (12.0 mmols) of the compound 3d as the dinitro component.

IR Spectrum [ν (cm$^{-1}$)]: 3416, 2336, 2200, 1590, 1506, 1474, 1404, 1342, 1272, 1170, 1052, 800, 658, 590; $^1$H-NMR Spectrum [δ (ppm)]: 1.23(m, 9H), 1.53(2H, m), 1.64(2H, m), 1.85(2H, m), 3.32(4H, t, J=7.4 Hz), 3.42(m, 8H), 3.95(t, 2H, J=6.3 Hz), 6.19(dd, 1H, J=2.3 Hz, 8.0 Hz), 6.25(d, 1H, J=2.3 Hz), 6.62(m, 6H), 6.94(d, 1H, J=16.0 Hz), 7.02(d, 1H, J=16.0 Hz), 7.05(d, 1H, J=4.1 Hz), 7.33(d, 2H, J=8.7 Hz), 7.43(d, 2H, J=9.0 Hz), 7.63(d, 1H, J=4.1 Hz)

Synthesis Example 31: Synthesis of polyimide precursor

A polyimide precursor solution was obtained in an amount of 10.7 g (solid content: 15% by weight) in the same manner as in Synthesis Example 5, but using 1.0 g (1.55 mmols) of the compound 4d as the diamine.

Synthesis Example 32: Synthesis of polyimide precursor copolymer

A polyimide precursor copolymer solution having a dye density of 20.0% was obtained in an amount of 28.9 g (solid content: 15% by weight) in the same manner as in Synthesis Example 6(2), but using 12.0 g of the polyimide precursor solution obtained in Synthesis Example 31 and 19.4 g of a polyimide precursor solution obtained in the same manner as in Synthesis Example 6(1). The stirring at 65° C. was carried out for 2 hours.

Synthesis Example 33: Formation of polyimide film

Heat curing was carried out in the same manner as in Synthesis Example 9, but using the polyimide precursor solution obtained in Synthesis Example 31. As a result, a film consisting of the polyimide having a repeating unit represented by the following chemical formula (18) was obtained.

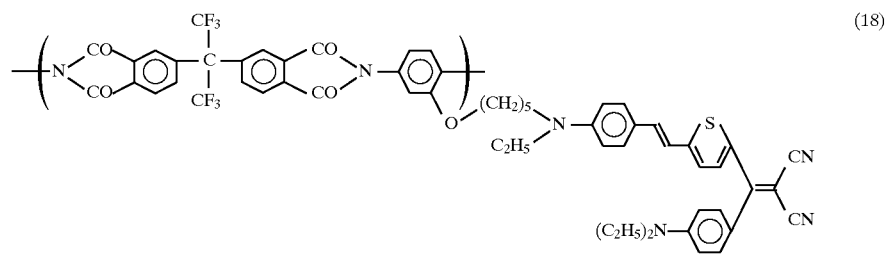

(18)

Example 5: Formation of polyimide copolymer film

Heat curing was carried out in the same manner as in Example 1, but using the polyimide precursor solution obtained in Synthesis Example 32. As a result, a film consisting of the polyimide having the repeating unit represented by the above chemical formula (18) and the repeating unit represented by the chemical formula (15) and having a dye density of 20.0% was formed. Characteristics of the polyimide film thus obtained were measured to obtain the results as shown in Table 1.

V. Synthesis of Polyimide Precursor or Polyimide
(n=6)

Synthesis Example 34: Synthesis of compound 1e (1) Synthesis of N-ethyl-N-(6-hydroxyhexyl)-4-bromoaniline Synthesized in the same manner as the step (3) in Synthesis Example 1, but from 10.0 g (49.9 mmols) of N-ethyl- 4-bromoaniline and 8.1 ml (1.2-fold equivalent weight) of 6-bromohexanol (amount: 11.1 g; yield: 74%).

IR Spectrum [ν (cm$^{-1}$)]: 3336, 2928, 2864, 1588, 1492, 1362, 1266, 1188, 1046, 798; $^1$H-NMR Spectrum [δ (ppm)]: 1.12(t, 3H, J=7.0 Hz), 1.37(m, 5H), 1.57(m, 4H), 3.21(t, 2H, J=7.6 Hz), 3.33(q, 2H, J=7.0 Hz), 3.64(t, 2H, J=6.4 Hz), 6.50(d, 2H, J=8.9 Hz), 7.23(d, 2H, J=8.9 Hz)

(2) Synthesis of N-ethyl-N-[6-(tetrahydropyran-2-yl)oxyhexyl]-4-bromoaniline:

A crude compound was obtained in an amount of 16.1 g (theoretical amount: 14.1 g) in the same manner as the step (4) in Synthesis Example 1, but from 11.0 g (36.6 mmols) of N-ethyl-N-(6-hydroxyhexyl)-4-bromoaniline.

IR Spectrum [ν (cm$^{-1}$)]: 2924, 1588, 1492, 1348, 1260, 1174, 1116, 1066, 1022, 906, 864, 800; $^1$H-NMR Spectrum [δ (ppm)]: 1.12(t, 3H, J=7.0 Hz), 1.35–1.95(m, 14H), 3.20(t, 2H, J=7.6 Hz), 3.27–3.51(m, 4H), 3.73(m, 1H), 3.86(m, 1H), 4.57(t, 1H, J=3.6 Hz), 6.50(d, 2H, J=9.1 Hz), 7.24(d, 2H, J=9.1 Hz)

(3) Synthesis of N-ethyl-N-[6-(tetrahydropyran-2-yl)oxyhexyl]-4-formylaniline:

Synthesized in the same manner as the step (5) in Synthesis Example 1, but using 16.1 g (theoretical amount: 14.1 g; theoretical molar number: 36.6 mmols) of the crude N-ethyl-N-[6-(tetrahydropyran-2-yl)oxyhexyl]-4-bromoaniline obtained in the step (2) (amount: 10.7 g; yield: 88%).

IR Spectrum [ν (cm$^{-1}$)]: 2924, 2724, 1664, 1592, 1554, 1526, 1436, 1402, 1352, 1312, 1274, 1236, 1154, 1072, 1020, 808; $^1$H-NMR Spectrum [δ (ppm)]: 1.20(t, 3H, J=7.0 Hz), 1.45–1.90(m, 14H), 3.30–3.52(m, 6H), 3.70–3.90(m, 2H), 4.75(s, 1H), 6.65(d, 2H, J=8.7 Hz), 7.70(d, 2H, J=8.7 Hz), 9.69(s, 1H)

(4) Synthesis of 2-{N-ethyl-N-[6-(tetrahydropyran-2-yl)oxyhexyl]anilin-4-yl}vinylthiophene:

Synthesized in the same manner as the step (6) in Synthesis Example 1, but using 10.5 g (31.5 mmols) of N-ethyl-N-[6-(tetrahydropyran-2-yl)oxyhexyl)-4-formylaniline as the formyl component (amount: 13.1 g; yield: quantitative).

IR Spectrum [ν (cm$^{-1}$)]: 2928, 2860, 1600, 1512, 1452, 1350, 1258, 1170, 1118, 1068, 1020, 946, 808, 680; $^1$H-NMR Spectrum [δ (ppm)]: 1.15(t, 3H, J=7.0 Hz), 1.38–1.45(m, 4H), 1.45–1.84(m, 10H), 3.26(t, 2H, J=7.56 Hz), 3.32–3.54(m, 4H), 3.74(m, 1H), 3.86(m, 1H), 4.57(t, 1H, J=3.4 Hz), 6.66(d, 2H, J=8.8 Hz), 6.85(d, 1H, J=16.8 Hz), 6.97(s, 2H), 7.01(d, 1H, J=16.8 Hz), 7.16(m, 1H), 7.32(d, 2H, J=8.8 Hz)

(5) Synthesis of compound 1e:

Compound 1e was obtained in an amount of 14.9 g (yield: 75%) in the same manner as the step (8) in Synthesis Example 1, but using 12.9 g (31.3 mmols) of 2-{N-ethyl-N-[6-(tetrahydropyran-2-yl)oxyhexyl]anilin-4-yl}vinylthiophene as the thiophene component.

IR Spectrum [ν (cm$^{-1}$)]: 2932, 2196, 1592, 1506, 1470, 1402, 1346, 1268, 1170, 1060, 1024, 796; $^1$H-NMR Spectrum [δ (ppm)]: 1.23(9H, m), 1.38–1.84(14H, m), 3.28(2H, t, J=7.9 Hz), 3.35–3.54(8H, m), 3.74(1H, m), 3.87(1H m), 4.57(1H, t, J=3.4 Hz), 6.62(2H, d, J=8.3 Hz), 6.67(2H, t, J=9.1 Hz), 6.94(d, 1H, J=15.9 Hz), 7.02(d, 1H, J=15.9 Hz), 7.05(1H, d, J=4.1 Hz), 7.33(2H, d, J=8.3 Hz), 7.43(2H, d, J=9.1 Hz), 7.63(1H, d, J=4.1 Hz)

Synthesis Example 35: Synthesis of compound 2e

Compound 2e was obtained in an amount of 12.8 g (yield: quantitative) in the same manner as in Synthesis Example 2, but using 14.5 g (22.8 mmols) of the compound 1e as the tetrahydropyranyl component.

IR Spectrum [ν (cm$^{-1}$)]: 3420, 2908, 2620, 2332, 1584, 1506, 1468, 1400, 1336, 1296, 1260, 1152, 1046, 946, 790; $^1$H-NMR Spectrum [δ (ppm)]: 1.21(m, 6H), 1.40(m, 4H), 1.58(m, 4H), 3.28(t, 2H, J=7.6 Hz), 3.42(m, 6H), 3.65(t, 2H, J=6.4 Hz), 6.61(d, 2H, J=8.9 Hz), 6.66(d, 2H, J=9.0 Hz), 6.93(d, 1H, J=15.9 Hz), 7.01(d, 1H, J=15.9 Hz), 7.04(d, 1H, J=4.2 Hz), 7.33(d, 2H, J=8.9Hz), 7.43(d, 2H, J=9.0 Hz), 7.62(d, 1H, J=4.2 Hz)

Synthesis Example 36: Synthesis of compound 3e

A crude compound 3e was obtained in an amount of 10.7 g (theoretical amount: 8.7%) in the same manner as in Synthesis Example 3, but using 6.69 g (12.1 mmols) of the compound 2e as the alcohol component.

IR Spectrum [ν (cm$^{-1}$)]: 3244, 2928, 2348, 2200, 1748, 1694, 1592, 1522, 1474, 1402, 1340, 1246, 1184, 1054, 796, 726, 588; $^1$H-NMR Spectrum [δ (ppm)]: 1.22(m, 12H), 1.42–1.69(m, 6H), 1.91(m, 2H), 3.32(t, 2H, J=7.4Hz), 3.45 (m, 6H), 4.27(m, 6H), 6.38(s, 1H), 6.64(m, 4H), 6.94(d, 1H, J=16.0 Hz), 7.02(d, 1H, 16.0 Hz), 7.05(d, 1H, J=3.9 Hz), 7.33(d, 2H, J=8.7 Hz), 7.43(d, 2H, J=8.9 Hz), 7.63(d, 1H, J=3.9 Hz), 7.90(d, 2H, J=5.6 Hz)

Synthesis Example 37: Synthesis of compound 4e

Compound 4e was obtained in an amount of 5.4 g (yield: 56%) in the same manner as in Synthesis Example 4, but from 10.5 g (theoretical amount: 8.5 g, 11.9 mmols) of the crude compound 3e.

IR Spectrum [ν (cm$^{-1}$)]: 3360, 2928, 2320, 2200, 1592, 1508, 1470, 1404, 1338, 1272, 1168, 1052, 798; $^1$H-NMR Spectrum [δ (ppm)]: 1.23(m, 9H), 1.40–1.67(m, 6H), 1.82 (quint, 2H, J=6.9 Hz), 2.80–3.70(brs, 4H), 3.30(t, 2H, J=7.5 Hz), 3.43(6H, m), 3.94(t, 2H, J=6.3 Hz), 6.18(dd, 1H, J=2.3 Hz, 7.9 Hz), 6.25(d, 1H, J=2.3 Hz), 6.60(1H, d, J=7.9 Hz), 6.62(d, 2H, J=8.9 Hz), 6.67(t, 2H, J=9.1 Hz), 6.94(d, 1H, J=15.9 Hz), 7.02(d, 1H, J=15.9 Hz), 7.05(1H, d, J=4.2 Hz), 7.33(2H, d, J=8.9 Hz), 7.43(2H, d, J=9.1 Hz), 7.63(1H, d, J=4.2 Hz)

Synthesis Example 38: Synthesis of polyimide precursor

A polyimide precursor solution (solid content: 15% by weight) was obtained in the same manner as in Synthesis Example 5, but using 0.65 g (0.99 mmols) of the compound 4e as the diamine. The molecular weight of the polyimide precursor thus obtained was measured to find that MN was 2.47×10$^5$ and MW was 4.32×10$^5$ in terms of polystyrene (elution time: 24.883 minutes; MW/MN=1.75).

Synthesis Example 39: Synthesis of polyimide precursor copolymer (dye density: 12.2%)

10.4 g of the polyimide precursor solution obtained in Synthesis Example 38 and 30.8 g of a polyimide precursor solution obtained in the same manner as in Synthesis Example 6(1) were mixed, and the mixture obtained was stirred at room temperature for 2 hours, followed by stirring at 80° C. for 30 minutes. The varnish thus obtained was pressure-filtered (filter: 0.22 μm in pore diameter) to obtain a polyimide precursor copolymer solution having a dye density of 12.2% (solid content: 15% by weight) (yield: 96%). The molecular weight of the polyimide precursor copolymer thus obtained was measured and it was found that MN was 6.79×10$^5$ and MW was 1.72×10$^6$ in terms of polystyrene (elution time: 22.639 minutes; MW/MN=2.53).

Synthesis Example 40: Synthesis of polyimide precursor copolymer (dye density: 20.0%)

A polyimide precursor copolymer solution having a dye density of 20.0% (solid content: 15% by weight) was obtained in an amount of 29.9 g in the same manner as in Synthesis Example 32, but using 12.0 g of the polyimide precursor solution obtained in Synthesis Example 38 and 20.2 g of a polyimide precursor solution obtained in the same manner as in Synthesis Example 6(1).

Synthesis Example 41: Formation of polyimide film

Heat curing was carried out in the same manner as in Synthesis Example 9, but using the polyimide precursor solution obtained in Synthesis Example 38. As a result, a film consisting of the polyimide having a repeating unit represented by the following chemical formula (19) was obtained.

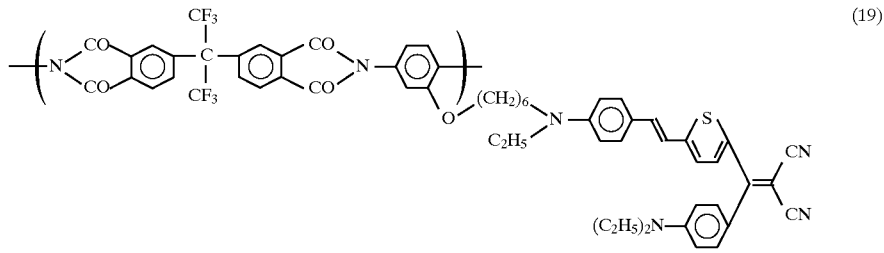

(19)

Example 6: Formation of polyimide copolymer film

A film consisting of the polyimide having the repeating unit represented by the above chemical formula (19) and the repeating unit represented by the chemical formula (15) and having a dye density of 20.0% was formed in the same manner as in Example 1, but using the polyimide precursor solution obtained in Synthesis Example 40, and its characteristics were measured. The results of measurement are shown in Table 1.

VI. Preparation of Resin Composition by Dopant Process

Example 7: Formulation of polyimide resin composition (1) Preparation of varnish:

To 20.0 g (solid content: 15% by weight) of a polyimide resin precursor synthesized in the same manner as in Synthesis Example 6(1), a solution prepared by dissolving 450 mg of the compound 2a in 6.1 g of N,N-diemthylacetamide was added, and the mixture was stirred at room temperature for 2 hours. Thereafter, the mixture obtained was pressure-filtered using a filter (pore diameter: 0.22 μm) to obtain a 24.7 g (solid content: 15% by weight) of a polyimide precursor copolymer composition having a dye density of 13.0%. Here, assuming the total weight of solid content as 100, the proportion (%) of the weight of atomic groups held therein, obtained by excluding oxygen atoms from the atomic groups of the compound of Formula (5), is regarded as dye density.

(2) Formation of resin film:

Heat curing was carried out in the same manner as in Synthesis Example 8, but using the polyimide precursor composition obtained in the above (1). As a result, a film consisting of the polyimide composition having a dye density of 13.0% was obtained. Characteristics of the polyimide composition film were measured to obtain the results shown in Table 1.

Example 8: Formulation of polymethacrylate resin composition (1) Preparation of varnish:

900 mg of poly(methyl methacrylate) was dissolved in 9 g of chloroform, and 100 mg of the compound 2a was added thereto, followed by mixing at room temperature for 2 hour to dissolve them. The mixture thus obtained was pressure-filtered using a filter (pore diameter: 0.22 μm) to obtain 9.5 g (solid content: 10% by weight) of a resin composition having a dye density of 10.0%.

(2) Formation of resin film:

The resin composition obtained in the above (1) was spin-coated on a silicon wafer of 5 inches diameter, having a surface formed of a silicon oxide layer, followed by drying. As a result, a film consisting of the poly(methyl methacrylate) composition having a dye density of 10.0% was obtained. Characteristics of the polymethyl methacrylate composition film were measured and the results shown in Table 1 were obtained.

VII. Production of Optical Device

Example 10: Production of Mach-Zehnder type waveguide switch (1) First, on the surface of a 6 inch silicon wafer 101 [FIG. 2 (a)], an aluminum type metal film 102a (thickness: 0.1 μm) was formed [FIG. 2 (b)], and a resist 103 was coated on its surface, followed by exposure and development to form the resist into a pattern [FIG. 2 (c)]. Thereafter, the metal layer 102a was etched and the resist was stripped off to form a lower electrode 102 [FIG. 2 (d)].

(2) Next, a polyimide precursor solution (having a TM refractive index of 1.599 after heat curing) was spin-coated on the surface of the wafer 101 so as to cover the lower electrode 102, followed by heat curing to form a polyimide layer 104a [FIG. 2 (e)]. A resist was coated on the surface of this polyimide layer 104a, and the resist coated was exposed in a stated pattern, followed by development [FIG. 2 (f)]. Thereafter, the polyimide layer 104a was etched and the resist was stripped off to form a lower clad layer 104b having concave portions corresponding to the core pattern of a Mach-Zehnder type waveguide switch [FIG. 2 (g)].

(3) In order to cover the concaves, the polyimide precursor copolymer solution obtained in Synthesis Example 6 was spin-coated on the surface of the lower clad layer 104b, followed by heating at 110° C. for 5 minutes, 280° C. for 15 minutes and at 295° C. for 10 minutes to cure to form a polyimide layer 106a [FIG. 2 (h)]. Thereafter, the surface of the polyimide layer 106a was abraded until the lower clad layer 104b was laid bare. Thus, a core 106 of the core pattern of a Mach-Zehnder type waveguide was formed [FIG. 2 (i)].

(4) In order to cover the core 106, the same polyimide precursor solution as used in the step (2) was spin-coated, followed by heat curing to form an upper clad layer to make it integral with the lower clad layer 104b already formed [FIG. 2 (j)]. Thus, the surface of the core 106 was covered with the clad layer 104.

(5) Next, on the surface of the clad layer 104, an aluminum type metal film 107a (1.0 μm) was formed [FIG. 2 (k)], and a resist 103 was coated on its surface, followed by exposure and development to form the resist into a pattern [FIG. 2 (l)]. Thereafter, the metal layer 107a was etched and the resist was stripped off to form an upper electrode 107

[FIG. 2 (*m*)]. Finally, the clad layer surface was coated with resin so as to cover the upper electrode 107, to provide a cover coat layer 108.

(6) The resulting wafer was subjected to poling, and thereafter a protective layer was spin-coated, followed by heat curing and then dicing, and the protective film was stripped off to obtain a Mach-Zehnder type waveguide switch.

The compound, polymer and polymer composition having a nonlinear optical ability, obtained in the present invention, can be used in optical devices such as optical switches for processing optical signals, e.g., branching, combining or amplifying them when, in photoelectric hybrid circuits, information is exchanged between operation elements and memories using optical wiring.

They can also be used in active optical waveguide devices employing optical waveguides in signal transmission lines so as to have a switching function (active function), as optical devices used in optical long-distance communication, signal processing, photoelectric hybrid circuits, optical computers and so forth.

In the field of optical recording, they can also be applied to wavelength conversion devices that utilize higher-harmonic generation attributable to nonlinear optical effects to convert wavelengths of lasers.

We claim:

1. An organic polymer comprising a first atomic group represented by the Formula (5):

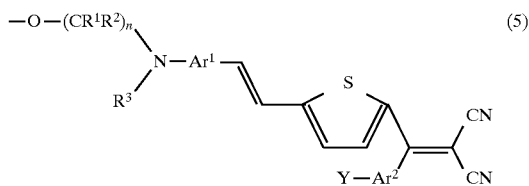

wherein $Ar^1$ and $Ar^2$ each independently represent an aromatic group or an aromatic group having a substituent, $R^1$, $R^2$ and $R^3$ each represent a hydrogen atom or a monovalent organic group, Y represents a hydrogen atom or a monovalent functional group, and n represents an integer of 2 to 10.

2. The organic polymer according to claim 1, further comprising a second atomic group represented by the following Formula (6):

wherein $Ar^3$ represents an aromatic group or an aromatic group having a substituent, and $Ar^3$ being combined with said first atomic group.

3. The organic polymer according to claim 1, which is an polymethacrylate having said atomic group as a side chain of its molecule.

4. The organic polymer according to claim 1, which is a polyimide or a precursor thereof.

5. The organic polymer according to claim 2, which is a polyimide or a precursor thereof.

6. An organic polymer produced from a material containing the diamine of Formula (4).

7. The organic polymer according to claim 6, which is a polyimide precursor obtained by allowing said diamine to react with a carboxylic anhydride.

8. The organic polymer according to claim 7, wherein said carboxylic anhydride is a compound represented by the following Formula (7):

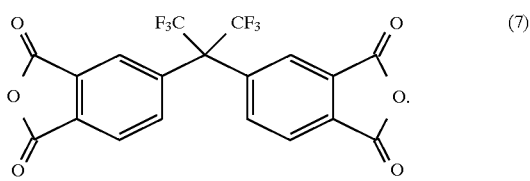

9. The organic polymer according to claim 6, which is a polyimide obtained by allowing said diamine to react with a carboxylic anhydride.

10. The organic polymer according to claim 9, wherein said carboxylic anhydride is a compound represented by the following Formula (7):

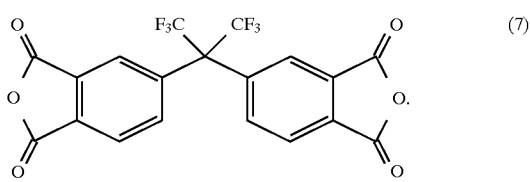

11. An organic copolymer produced by mixing and heating a first polyimide precursor and a second polyimide precursor;

said first polyimide precursor being obtained by allowing the diamine of Formula (4) to react with a carboxylic anhydride.

12. The organic copolymer according to claim 11, wherein said second polyimide precursor has a repeating unit represented by the following Formula (8):

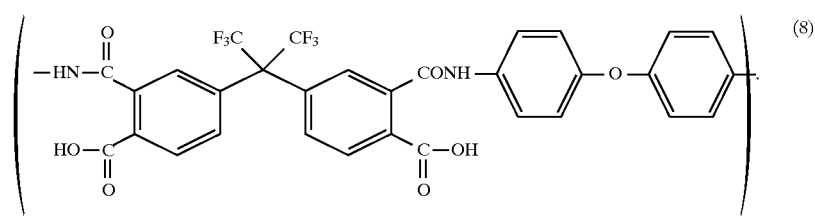

13. A polyimide copolymer produced by curing the organic copolymer of claim 11.

14. A resin precursor composition comprising at least one of a heteroaromatic compound represented by the following Formula (1) or (2), a dinitro compound represented by the following Formula (3) and a diamine represented by the following Formula (4):

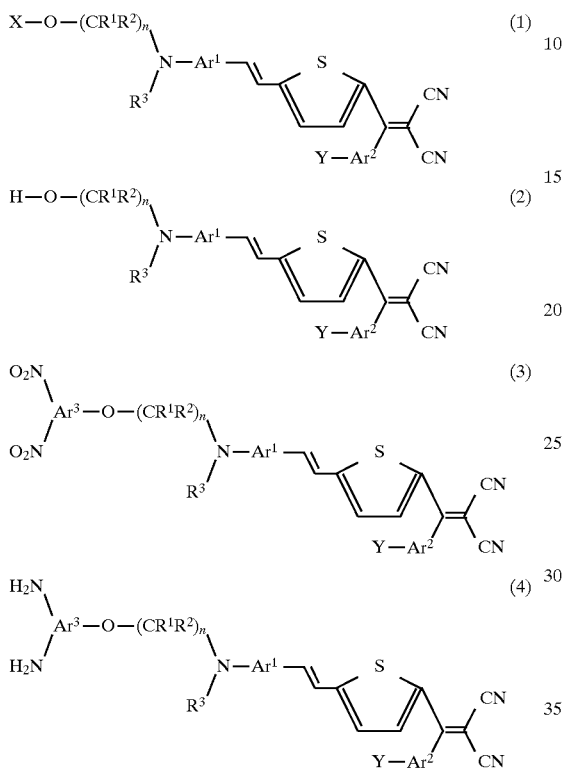

wherein $Ar^1$, $Ar^2$ and $Ar^3$ each independently represent an aromatic group or an aromatic group having a substituent, $R^1$, $R^2$ and $R^3$ each represent a hydrogen atom or a monovalent organic group, X represents a monovalent organic group, Y represents a hydrogen atom or a monovalent functional group, and n represents an integer of 2 to 10.

15. A resin composition comprising:

an organic polymer; and at least one of a heteroaromatic compound represented by the following Formula (1) or (2), a dinitro compound represented by the following Formula (3) and a diamine represented by the following Formula (4):

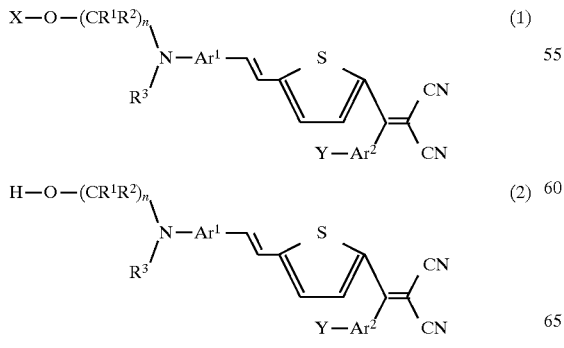

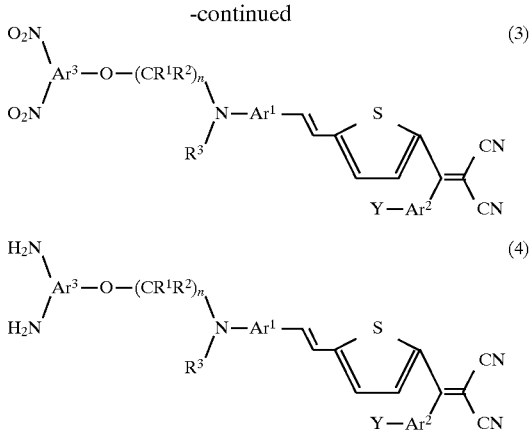

wherein $Ar^1$, $Ar^2$ and $Ar^3$ each independently represent an aromatic group or an aromatic group having a substituent, $R^1$, $R^2$ and $R^3$ each represent a hydrogen atom or a monovalent organic group, X represents a monovalent organic group, Y represents a hydrogen atom or a monovalent functional group, and n represents an integer of 2 to 10.

16. A resin composition having at least one of the following polymers (a) to (d):

(a) an organic polymer comprising an atomic group represented by the following Formula (5):

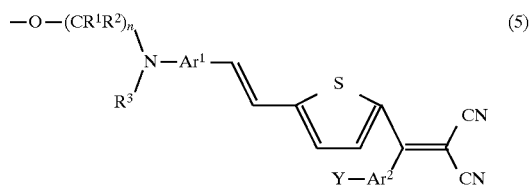

wherein $Ar^1$ and $Ar^2$ each independently represent an aromatic group or an aromatic group having a substituent, $R^1$, $R^2$ and $R^3$ each represent a hydrogen atom or a monovalent organic group, Y represents a hydrogen atom or a monovalent functional group, and n represents an integer of 2 to 10;

(b) a polyimide precursor or polyimide obtained by allowing a diamine represented by the following Formula (4) to react with a carboxylic anhydride:

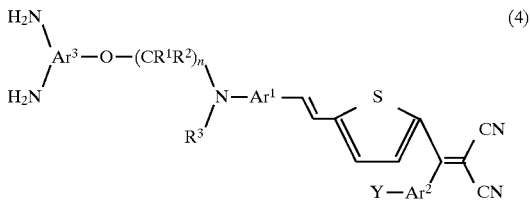

wherein $Ar^1$, $Ar^2$ and $Ar^3$ each independently represent an aromatic group or an aromatic group having a substituent, $R^1$, $R^2$ and $R^3$ each represent a hydrogen atom or a monovalent organic group, Y represents a hydrogen atom or a monovalent functional group, and n represents an integer of 2 to 10;

(c) a polyimide precursor copolymer produced by mixing and heating a first polyimide precursor which is obtained by allowing a diamine represented by the above Formula (4) to react with a carboxylic anhydride, and a second polyimide precursor; and (d) a polyimide copolymer produced by curing said polyimide precursor copolymer.

17. A nonlinear optical element obtained by curing the resin precursor composition of claim 14.

18. A nonlinear optical element consisting of the resin composition of claim 15.

19. A nonlinear optical element obtained by curing the resin composition of claim 16.

20. An optical device having the nonlinear optical element of claim 17.

21. An optical device having the nonlinear optical element of claim 18.

22. An optical device having the nonlinear optical element of claim 19.

23. A process for producing a nonlinear optical element, comprising a step of curing the resin precursor composition of claim 14.

24. A process for producing a nonlinear optical element, comprising a step of curing the resin composition of claim 16.

25. A process for producing an optical device, comprising a step of curing the resin precursor composition of claim 14 to form a nonlinear optical element.

26. A process for producing an optical device, comprising a step of curing the resin composition of claim 16 to form a nonlinear optical element.

* * * * *